US012357497B2

(12) United States Patent
Moscherosch et al.

(10) Patent No.: US 12,357,497 B2
(45) Date of Patent: *Jul. 15, 2025

(54) ARTICLE AND METHOD FOR MAINTAINING MENSTRUAL FLUID WITHIN THE VAGINA

(71) Applicant: Johnson & Johnson Consumer Inc., Skillman, NJ (US)

(72) Inventors: H. Michael Moscherosch, Doylestown, PA (US); Jennifer L Sturgeon, Long Valley, NJ (US); Mari Hou, Basking Ridge, NJ (US)

(73) Assignee: Kenvue Brands LLC, Summit, NJ (US)

( * ) Notice: Subject to any disclaimer, the term of this patent is extended or adjusted under 35 U.S.C. 154(b) by 514 days.

This patent is subject to a terminal disclaimer.

(21) Appl. No.: 16/867,156

(22) Filed: May 5, 2020

(65) Prior Publication Data

US 2020/0261253 A1    Aug. 20, 2020

Related U.S. Application Data

(63) Continuation of application No. 15/500,725, filed as application No. PCT/US2014/049045 on Jul. 31, 2014, now Pat. No. 10,758,397.

(51) Int. Cl.
*A61F 5/443*    (2006.01)
*A61F 5/455*    (2006.01)
(Continued)

(52) U.S. Cl.
CPC .............. *A61F 5/443* (2013.01); *A61F 5/455* (2013.01); *A61F 13/15203* (2013.01);
(Continued)

(58) Field of Classification Search
CPC ...................... A61F 5/443; A61F 5/455; A61F 2013/15569; A61F 2013/15471; A61F 2013/15373; A61F 2013/15365; A61F 13/82; A61F 13/472; A61F 13/15203; A61F 13/47209
See application file for complete search history.

(56) References Cited

U.S. PATENT DOCUMENTS 3,019,443 A * 2/1962 Lewis .................. A41D 27/133
2/55
3,802,817 A    4/1974 Matsuki et al.
(Continued)

FOREIGN PATENT DOCUMENTS

CN    103961217 A    8/2014
EP    120570 A    10/1984
(Continued)

OTHER PUBLICATIONS

International search report dated May 7, 2015, for international application PCT/US2014/049045.

*Primary Examiner* — Ariana Zimbouski

(57) ABSTRACT

The present invention relates to sanitary protection article that is structured and arranged to maintain menstrual fluid within the vagina and thereby prevent the menstrual fluid from escaping the body. The present invention also relates to a method of selectively maintaining menstrual fluid within the vagina by means of using such article.

17 Claims, 3 Drawing Sheets

(51) Int. Cl.
*A61F 13/15* (2006.01)
*A61F 13/472* (2006.01)
*A61F 13/82* (2006.01)

(52) U.S. Cl.
CPC ............ *A61F 13/472* (2013.01); *A61F 13/82* (2013.01); *A61F 2013/15365* (2013.01); *A61F 2013/15373* (2013.01); *A61F 2013/15471* (2013.01); *A61F 2013/15569* (2013.01)

(56) References Cited

U.S. PATENT DOCUMENTS

| | | | |
|---|---|---|---|
| 3,855,046 | A | 12/1974 | Hansen et al. |
| 4,231,369 | A | 11/1980 | Sorensen et al. |
| 4,340,563 | A | 7/1982 | Appel et al. |
| 4,367,732 | A | 1/1983 | Poulsen et al. |
| 4,372,303 | A | 2/1983 | Grossmann et al. |
| 4,374,888 | A | 2/1983 | Bornslaeger |
| 4,485,809 | A | 12/1984 | Dellas |
| 4,513,739 | A | 4/1985 | Johns |
| 4,522,203 | A | 6/1985 | Mays |
| 4,661,099 | A * | 4/1987 | von Bittera ............ A61L 15/58 428/355 R |
| 4,692,618 | A | 9/1987 | Klatt |
| 4,734,324 | A | 3/1988 | Hill |
| 4,777,073 | A | 10/1988 | Sheth |
| 4,867,748 | A | 9/1989 | Samuelsen |
| 4,867,881 | A | 9/1989 | Kinzer |
| 4,991,574 | A | 2/1991 | Pocknell |
| 5,059,282 | A | 10/1991 | Ampulski et al. |
| 5,085,884 | A | 2/1992 | Young et al. |
| 5,088,483 | A | 2/1992 | Heinecke |
| 5,114,419 | A * | 5/1992 | Daniel ..................... A41B 9/00 604/385.15 |
| 5,145,933 | A | 9/1992 | Grisoni et al. |
| 5,174,927 | A | 12/1992 | Honsa |
| 5,236,733 | A | 8/1993 | Zimmerman et al. |
| 5,248,309 | A | 9/1993 | Serbiak et al. |
| 5,382,400 | A | 1/1995 | Pike et al. |
| 5,422,131 | A | 6/1995 | Elsen et al. |
| D369,907 | S | 5/1996 | Sayovitz et al. |
| 5,599,289 | A * | 2/1997 | Castellana ............ A61F 13/023 128/853 |
| 5,618,281 | A | 4/1997 | Betrabet et al. |
| 5,620,779 | A | 4/1997 | Levy et al. |
| 5,635,134 | A | 6/1997 | Bourne et al. |
| 5,669,395 | A * | 9/1997 | Thompson ............ A61F 13/145 128/857 |
| 5,695,484 | A * | 12/1997 | Cox ..................... A61F 2/0009 604/304 |
| 5,695,868 | A | 12/1997 | McCormack |
| D390,798 | S | 2/1998 | Kobayashi |
| 5,714,107 | A | 2/1998 | Levy et al. |
| 5,714,225 | A | 2/1998 | Hansen et al. |
| 5,800,758 | A | 9/1998 | Topolkaraev et al. |
| 5,855,999 | A | 1/1999 | McCormack |
| 5,858,519 | A | 1/1999 | Klinger et al. |
| 5,927,282 | A * | 7/1999 | Lenker ............ A61F 13/47209 128/885 |
| 6,045,900 | A | 4/2000 | Haffner et al. |
| 6,075,179 | A | 6/2000 | McCormack et al. |
| 6,585,997 | B2 | 7/2003 | Moro et al. |
| 6,909,028 | B1 | 6/2005 | Shawver et al. |
| 7,514,591 | B2 * | 4/2009 | Przepasniak ...... A61F 13/15211 604/385.01 |
| 7,811,272 | B2 | 10/2010 | Lindsay et al. |
| 7,880,051 | B2 | 2/2011 | Madsen et al. |
| 2003/0187115 | A1 | 10/2003 | Cinelli et al. |
| 2003/0191442 | A1* | 10/2003 | Bewick-Sonntag ........................ A61F 13/51305 604/385.18 |
| 2007/0100313 | A1* | 5/2007 | Luizzi ................... A61F 13/474 604/389 |
| 2007/0202245 | A1 | 8/2007 | Gantner et al. |
| 2009/0118691 | A1 | 5/2009 | Rosenfeld |
| 2009/0148503 | A1* | 6/2009 | Trieu ..................... A61B 17/42 424/447 |
| 2010/0198177 | A1* | 8/2010 | Yahiaoui ................. A61L 15/58 604/385.03 |
| 2011/0162661 | A1* | 7/2011 | St. Anne ............... A61L 24/001 128/885 |
| 2011/0251541 | A1* | 10/2011 | Kim ..................... A61L 15/425 602/46 |
| 2012/0004633 | A1 | 1/2012 | R. Marcelo et al. |
| 2015/0217098 | A1 | 8/2015 | Hicken et al. |
| 2015/0245679 | A1* | 9/2015 | Leete ................... A41D 27/133 2/55 |
| 2017/0027767 | A1 | 2/2017 | Hengsberger et al. |
| 2020/0022834 | A1* | 1/2020 | VanPelt .................. A61F 13/82 |

FOREIGN PATENT DOCUMENTS

| | | |
|---|---|---|
| WO | WO 1996/038115 A | 12/1996 |
| WO | WO 1998/023804 A | 6/1998 |
| WO | WO 1999/026576 A | 6/1999 |
| WO | WO 1999/039036 A | 8/1999 |
| WO | WO 2002/028447 A | 4/2002 |
| WO | WO 2008/057155 A | 5/2008 |
| WO | WO 2010/077306 A | 7/2010 |
| WO | WO 2011/110878 A | 9/2011 |
| WO | WO 2011/121303 A | 10/2011 |
| WO | WO 2014/003957 A | 1/2014 |

* cited by examiner

ARTICLE AND METHOD FOR MAINTAINING MENSTRUAL FLUID WITHIN THE VAGINA

CROSS-REFERENCE TO RELATED APPLICATIONS

This application is a continuation of U.S. patent application Ser. No. 15/500,725 filed on Jan. 31, 2017, which is the national stage filing under 35 USC 371 of international application PCT/US2014/049045 filed on Jul. 31, 2014, the complete disclosures of which are hereby incorporated herein by reference for all purposes.

FIELD OF INVENTION

The present invention relates to a sanitary protection article that is structured and arranged to maintain menstrual fluid within the vagina and thereby prevent the menstrual fluid from escaping the body. The present invention also relates to a method of selectively maintaining menstrual fluid within the vagina by means of using such article.

BACKGROUND OF THE INVENTION

A variety of externally worn sanitary absorbent articles are known in the art, such as, for example, sanitary napkins and liners. Such articles typically include a liquid permeable cover layer, a liquid impermeable barrier layer and an absorbent core arranged between the cover layer and barrier layer. These articles primary mode of operation is to absorb the menstrual fluid after such fluid escapes from the body.

Body-attachable sanitary absorbent articles are also known, such as for example body-attachable sanitary napkins. These articles are structured in much the same way as conventional sanitary napkins but further include an adhesive arranged on the body-facing surface of the article that allows the article to be selectively attached to the body. Although these body-attachable articles are placed in close proximity to the vaginal opening, their primary mode of operation is the same as a conventional napkin, that is, they absorb menstrual fluid as it escapes from the vaginal opening.

Other known sanitary absorbent articles are adapted to be arranged either partially within the vagina (e.g. certain interlabial articles) or entirely within the vagina (e.g. tampons). Although these devices are adapted to be inserted within the vagina, their basic mode of operation is the same as a napkin. That is, the article is adapted to absorb menstrual fluid.

A problem with all of the articles described above is that the effectiveness of the article is limited by the fluid handling capabilities of the article. To provide adequate protection, absorbency of the articles must be sufficient so as to prevent fluid leakage. Products with such absorbency, however, tend to be large, bulky or otherwise uncomfortable. And, being absorbent, such products, under certain conditions, for example a particularly heavy menstrual flow, are subject to leakage and failure.

Another problem associated with absorbent type feminine articles relates to their use during activities requiring bodily contact with water (such as swimming). In such cases, extra fluids (e.g., water) are absorbed by the absorbent article in addition to any vaginal fluids, thereby increasing the discomfort of such absorbent articles to the user.

In view of the above, it is an aspect of the present invention to provide an article that overcomes the deficiencies of the prior art articles described above. In addition, it is an aspect of the present invention to provide an article that has a primary mode of operation that differs from the above described articles. Specifically, the article according to the present invention, as described in greater detail below, functions not by absorbing menstrual fluid but rather by maintaining menstrual fluid within the vagina thereby preventing the same from escaping the body. Another aspect of the present invention is to provide a non-absorbent or substantially non-absorbent article that is sized so as to be compact and unnoticeable or substantially unnoticeable by a user during use. A further aspect of the present invention is to provide an article which increases the confidence of the user that there will be no leakage of vaginal fluid or exudate after application of the article during athletic or otherwise strenuous activities.

SUMMARY OF THE INVENTION

In view of the foregoing the present invention provides, according to a first aspect of the invention, an article for maintaining menstrual fluid within the vagina, the article including a flexible substrate having a body facing surface and an opposed garment facing surface, adhesive applied to the body facing surface of the substrate for selectively adhering the article to the body, wherein the substrate is structured and arranged to cover the vaginal opening and thereby maintain menstrual fluid within the vagina.

The present invention provides, according to a second aspect of the invention, a method of maintaining menstrual fluid in the human body including the steps of applying an article to the body such that the article extends over the vaginal opening, wherein the article includes a flexible substrate having a body facing surface and an opposed garment facing surface, adhesive applied to the body facing surface of the substrate for selectively adhering the article to the body, wherein the substrate is structured and arranged to cover the vaginal opening and thereby maintain menstrual fluid within the vagina.

In certain embodiments, the present invention relates to an article for maintaining menstrual fluid within the vagina comprising:

a flexible substrate having a body facing surface and an opposed garment facing surface;

an adhesive selected from the group consisting of non-pressure sensitive adhesive substance, muco- or bioadhesive or mixtures thereof wherein the adhesive applied to the body facing surface of the substrate for selectively adhering the article to the body; and wherein the article is sized, structured and arranged to fit in the region on the internal side of the labia but external the vagina to directly cover the introitus and thereby maintain the menstrual fluid within the vagina.

BRIEF DESCRIPTION OF THE DRAWINGS

Examples of embodiments of the present invention will now be described with reference to the drawings, in which.

DETAILED DESCRIPTION OF THE INVENTION

Figure 7:
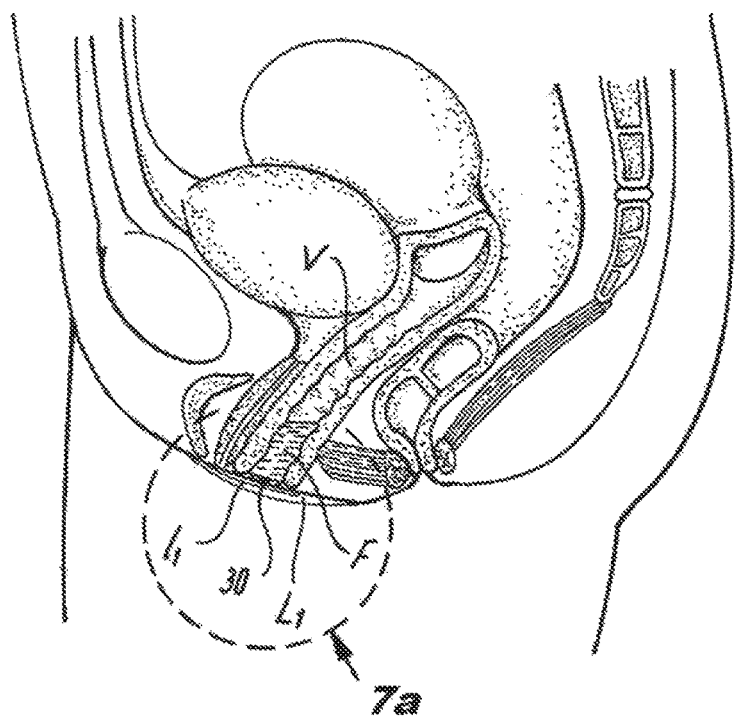
FIGS. 7 and 7a are schematic sectional views of the body depicting the manner in which the article is positioned in/on the inner labial mucosal region for covering the introitus to retain menstrual fluid within the vagina.
Figure 7A:
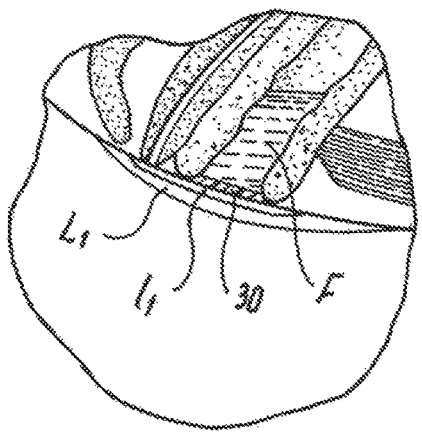

The present invention relates to a substantially non-absorbent article that is adapted to selectively maintain menstrual fluid within the vagina. As will be described in greater detail below, the article according to the present invention is intended to be applied to the body during menstruation such that the article extends over the vaginal opening. In one embodiment, the article is a labial adhesive patch 12 designed or adapted to contact, attach or adhere to the user's skin and functions to maintain menstrual fluid within the vagina. In one embodiment of the invention, the article is structured and arranged to extend from at least one labium minus to an opposed labium minus to maintain the labia minora in a closed configuration to thereby maintain the menstrual fluid within the vagina. In another embodiment of the invention, the article is an inner labial patch 30 structured, sized and arranged to fit in the region on the internal side of the labia but external the vagina to directly cover the introitus and thereby maintain the menstrual fluid within the vagina (as illustrated at FIGS. 7 and 7a; that region, hereinafter referred to as the "inner labial mucosal region"). When a user desires to release the menstrual fluid, the article is simply removed from the body and the menstrual fluid is released. Thereafter, the user may apply a new, clean, article.

In certain embodiments, the article according to the present invention is "non-absorbent" or "substantially non-absorbent". "Substantially non-absorbent" as used herein means the article has a total absorbent capacity of less than about 0.3 g, more preferably less than about 0.1 g, more preferably less than about 0.05 g. as measured using the Procedure for Measuring Absorbent Capacity described below.

In certain embodiments, the articles of the present invention have a Fluid Penetration Time (FPT), when measured by the Procedure for Measuring Fluid Penetration Time (FPT) as described below, of greater than 500 seconds, optionally 600 seconds, or optionally 700 seconds.

Since the article according to the present invention does not function by means of absorption (as exhibited by the low absorbent capacity and/or high Fluid Penetration Time (FPT) of the articles of the present invention [according to the test methods described below]), but rather functions by means of maintaining menstrual fluid within the body, the shortcomings of prior art articles such as sanitary napkins, liners, tampons and the like can be avoided.

Figure 1:
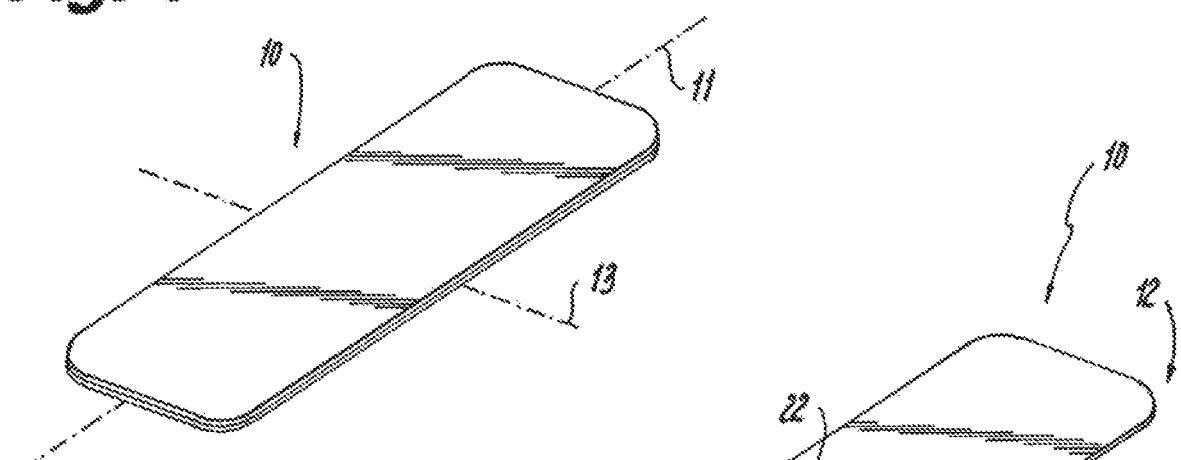
FIG. 1 is a perspective view of the article according to the present invention.
Figure 2:
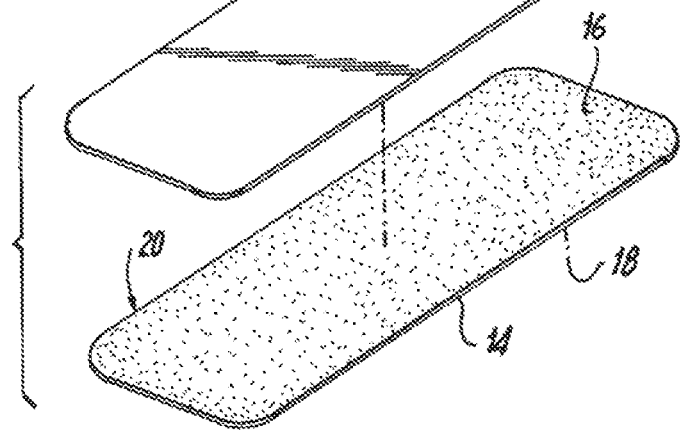
FIG. 2 is a partially exploded perspective view of the article shown in FIG. 1.

Reference is made to FIGS. 1 and 2 which depict an article 10 according to one embodiment of the present invention. The article 10 includes a longitudinally extending centerline 11 and a transversely extending centerline 13. In the particular embodiment of the invention shown in FIGS. 1 and 2 the article 10 generally comprises a labial adhesive patch 12 that is formed from a flexible substrate material 14. The substrate material 14 includes a body-facing surface 16 and an opposed garment facing surface 18. The body-facing surface 16 of the substrate material 14 is provided with an adhesive 20 that is adapted to enable a user to selectively apply and remove the labial adhesive patch 12 to the body in a hurt-free manner. The adhesive 20 preferably extends over about 5% to about 100% the surface area of the body-facing surface 16.

In certain embodiments, the article 10 according the present invention can be in the form of a labial adhesive patch 12 (i.e., for application to the skin of the vaginal region) or an inner labial patch 30 (i.e., for application in the inner labial mucosal region directly cover the introitus) and preferably has a thickness (not including any release paper) in the range of about 0.01 mm to about 5.0 mm, optionally about 0.5 mm to about 1 mm, or optionally about 0.3 to about 0.9, when measured using an Ames Micrometer (B.C. Ames Inc., Waltman, Mass., Model ADP 1132, 175 g on the 1⅛"=0.384 psi). For purposes of determining thickness, the thickness measurements are taken over the portion (or area) of the article 10 to be positioned over the introitus.

In certain embodiments, article 10 can have a basis weight of at least 2 g/m², optionally, basis weight between about 5 g/m² and about 150 g/m². The article 10 according to the embodiment shown in FIG. 1 generally has a substantially rectangular shape, although other shapes are possible, such as for example a square, a circle, an oval shape or elliptical shape. Other more ornamental shapes (such as a butterfly shape) can also be used. In addition, although a symmetrical configuration of the article is depicted in the drawings other asymmetrical shapes are possible.

Preferably, the article 10 has a length as measured along the longitudinally extending center line 11 in the range of about 20 mm to about 150 mm. Preferably the article 10 has a width as measured along the transversely extending centerline 13 in the range of about 20 mm to about 100 mm. The article 10 preferably has a total surface area in the range of from about 400 mm² to about 15000 mm². The article 10 is depicted in the figures as having dimension that is greater in the longitudinally extending direction than in the transversely extending direction, i.e. it is longer than it is wide. However, specific configurations wherein the article is wider than it is long are also possible.

As shown in FIG. 2, the article 10 may be optionally provided with a removable release liner 22 that is adapted to cover and protect the adhesive 20 prior to use. The release liner may be constructed from paper, film, nonwovens and other suitable materials known to those of skill in the art. The release liner 22 may be provided with a non-stick coating to prevent the release paper 22 from adhering to the adhesive 20. The non-stick coating may be a material based on polydimethylsiloxane chemistries, generically referred to as "silicones". The non-stick coating may also be a material based on other non-silicone chemistries, such as fluropolymers, alkyds, carbamates, urethanes, chromium complexes, acrylics, poly vinyl alcohols, or olefins. In certain embodiments, the adhesiveness of release paper 22 to adhesive 20 is reduced or prevented by choosing release liner materials that vary the topography of the surface of release liner 22 so as to reduce the surface area of release liner 22 that contacts adhesive 20.

Although not depicted in the drawings, a stacked article configuration is possible. In certain embodiments for purposes of packaging, a plurality articles 10 could be arranged in stacked configuration one on top of the other. In such a stacked configuration, only the bottommost article would require a release liner. In other embodiments, a plurality of articles 10 comprising no more than 10, optionally no more than 5, optionally no more than 3 articles could be arranged in stacked configuration one on top of the other, allowing the user to have immediate access to a clean article 10 when an underlying one is soiled. In such a stacked configuration, only the body facing side (i.e., the side attached to the user) of the bottommost article would require a release liner. Once the release liner is removed, the body facing side of the stacked plurality of articles is attached to the user. Upon soiling of the bottommost article of the stacked plurality of articles, the stacked plurality of articles is removed from the user and the soiled bottommost article of the stacked plurality of articles is removed to expose the bodyfacing side of a clean bottommost article 10. The body facing side of the clean bottommost article 10 of the stacked plurality of articles is then reattached to the user.

Figure 3:
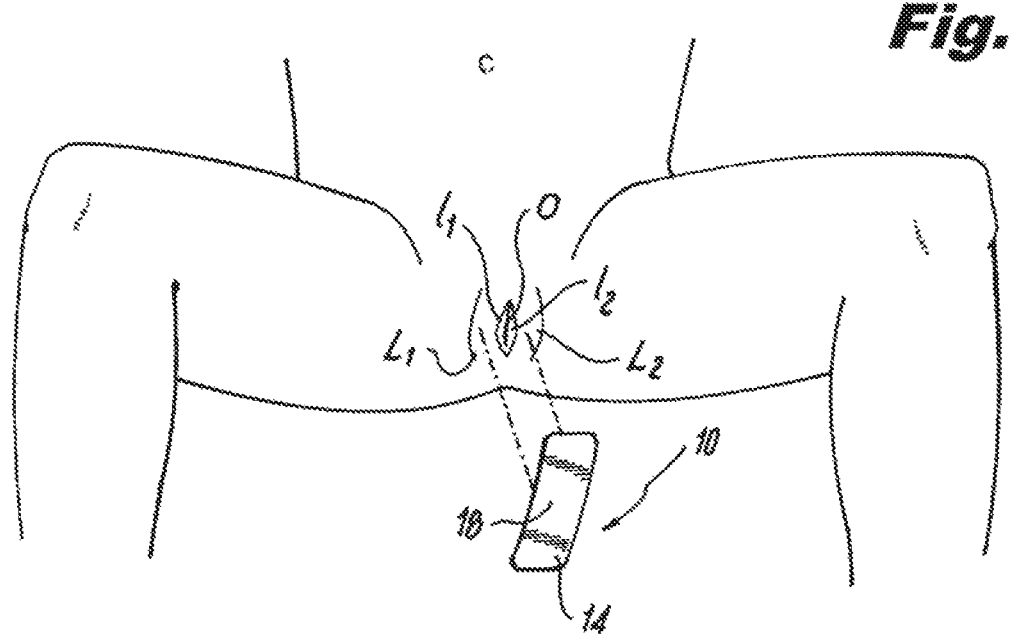
FIGS. 3 and 4 are schematic views depicting the manner in which the article is applied to the skin of a user's body, the article extending at least from one labium minus $l_1$ of labium majora $L_1$ to an opposed labium minus $l_2$ of labium majora $L_2$.
Figure 4:
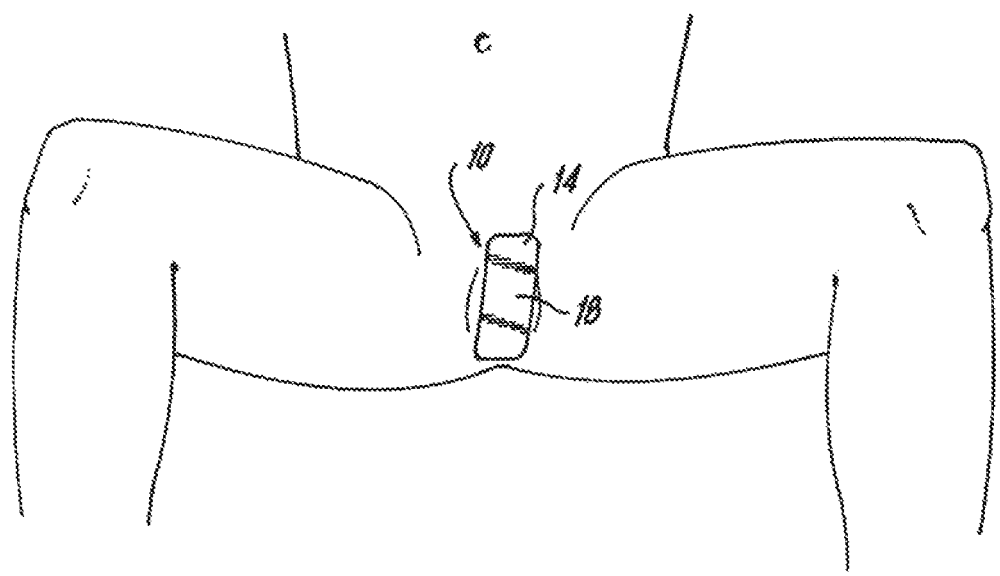
Figure 5:
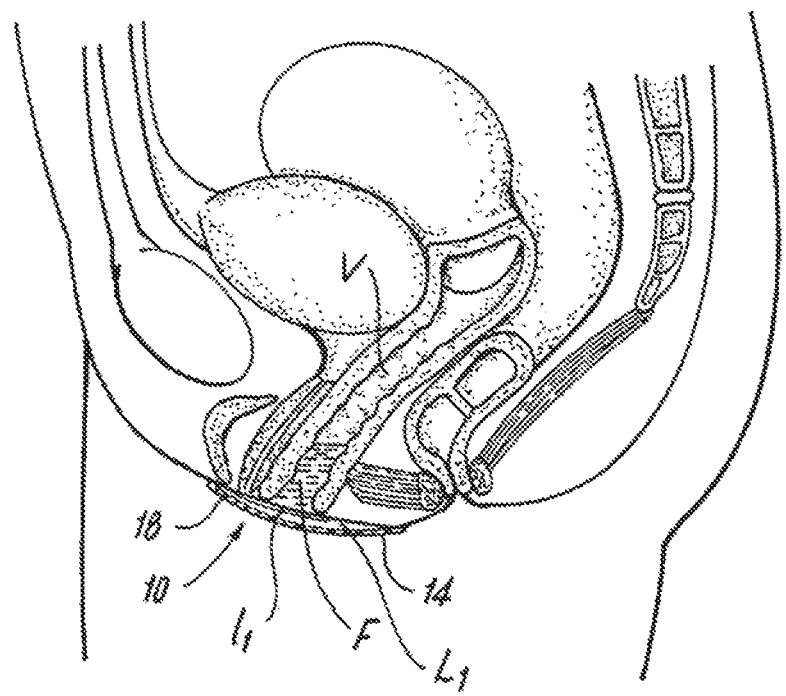
FIG. 5 is schematic sectional view of the body depicting the manner in which article maintains menstrual fluid within the vagina.

Reference is made to FIGS. 3-5 which depict the manner in which the article 10 is used. First, the user removes the release paper 22 from the substrate material 14 to thereby expose the adhesive 20.

Thereafter, as shown in FIG. 3, the article 10 is arranged over the vaginal opening "O" such that the substrate material 14 covers the vaginal opening and thereby functions to maintain menstrual fluid within the vagina. In one preferred embodiment depicted in the figures, the substrate 14 extends at least from the outer side of one labium minus $l_1$ of labium majora $L_1$ to the outer side of an opposed labium minus $l_2$ of labium majora $L_2$. Preferably, the article 10 is arranged such that the intersection of the longitudinally extending centerline 11 and transversely extending centerline 13 is substantially centered over the vaginal opening "O". In certain embodiments, the user may stretch the article from a non-stretched position to a stretched position across the labium minus $l_1$ and labium minus $l_2$ using a stretching force such that, upon adhesion of the article to the labia in such stretched position, release of the stretching force results in the adhered article returning to its non-stretched position and thereby causing labium minus $l_1$ and labium minus $l_2$ to be squeezed together. After the user places the article 10 in the proper location the user applies slight pressure to the garment facing surface 18 of the article 10 towards the body to thereby adhere the article 10 to the body. As shown in FIG. 5, the article 10 functions to maintain any discharged menstrual fluid "F" within the vagina "V" and prevents the fluid from escaping the body.

When the user desires to release the menstrual fluid "F" the user can simply remove the article 10 from the body and permit the natural release of the menstrual fluid "F". Thereafter the user may apply a new clean article 10 to the body in the same manner as described above. Furthermore, the user may apply at least one article 10 to the body, per day, for each day of the user's menstrual period. In this manner, the article 10 may be employed as an effective sanitary protection article.

Flexible Substrate Materials

The flexible substrate material 14 is preferably formed from a liquid impervious, substantially non-absorbent, flexible, elastic material. Such a material functions to maintain the menstrual fluid within the body during use of the article 10 and due to its liquid impervious, non-absorbent nature, functions to prevent fluid from passing through the substrate. In addition, since the material forming the substrate material 14 is elastic, the substrate material 14 is free to move with the body during use, elastically deform as necessary during movement of the body (including valsalva movements such as caused by coughing, sneezing and the like), and recover its original shape. Particularly suitable materials for use as the substrate material 14 include liquid impervious, substantially non-absorbent, flexible, elastic polymer film materials of the type commercially available from Tredegar Film Products, Lake Zurich, IL The flexible substrate material 14 may also be formed from non-permeable foams, such as polyurethane foam, polyethylene foam, and the like, in each case, with or without any additional barrier layers. Substantially non-absorbent, non-permeable hydrocolloid materials could also be employed. It is possible that phase-changing materials may also be employed as the substrate material 14. For example, a temperature responsive material could be employed that would enable the substrate material 14 to conform to the body during wear. Other body conforming materials could also be employed.

The flexibility of the articles of the present invention is determined using Gurley method, TAPPI T543 om-94. The lower the Gurley stiffness value, the more flexible the article. In certain embodiments, the article 10 has a Gurley stiffness of from about 300 mg (optionally about 200 mg, optionally about 100 mg, optionally about 50 mg, or optionally about 10 mg, or optionally 5 mg) to about 2 mg (optionally about 1 mg, or optionally about 0.5 mg) using the above Gurley method. In certain embodiments, the Gurley stiffness of the articles of the present invention is from 2 mg to 5 mg using the above Gurley method. The Gurley method is performed on the article in state (or condition) in which it is worn by the user (i.e., without a release liner or any other structural aid). Also, the adhesive surface should be detackified by a light coating of talcum powder or similar material (such as corn starch).

To some users an article capable of stretching and recovering with low applied force may be desirable so that during wear, the product will easily stretch with body motion and the user will not feel uncomfortable pulling sensations. The ease with which an article can be stretched is the article's tensile stretchability. The tensile stretchability of an article is determined using the Procedure for Measuring Tensile Stretchability as described below. In certain embodiments, the articles of the present invention have a tensile stretchability of from about 30 to about 150 N/meter of applied force to stretch to a 20% extension. Other users may prefer an article that is less stretchable so that the article will be able to more securely maintain the labium in a closed position. Accordingly, in other embodiments, the articles of the present invention have a tensile stretchability of greater than about 150 to about 5000 N/meter of applied force to stretch to a 20% extension.

By employing a flexible substrate material 14 of the type described above, the article 10 has the ability to elongate in both the transverse and longitudinal directions article by at least 35% when subjected to the types of loads that one would expect the article to be subjected to during normal use of the product. In addition, the article preferably recovers from such deformation by at least 90% when the load is removed, more preferably by at least 95% and most preferably by at least 98%. The above deformation and recovery properties of the article 10 allow the article 10 to move with the body yet at the same time recover its original shape after the force causing the deformation is removed.

In certain embodiments, the substrate material 14 comprises one or more layers of a breathable material. As used herein, the term "breathability" refers to the water vapor transmission rate (WVTR) of an area of fabric which is measured in grams of water per square meter per day ($g/m^2/24$ hours). The WVTR of a layer of material, in one aspect, gives an indication of how comfortable the material would be when applied to the user's skin or mucosal region. WVTR can be measured as indicated below. In certain embodiments, the substrate material 14 has a WVTR greater than 500 g/m²/day, and more desirably wherein the substrate material 14 has a WVTR in excess of about 1000 g/m²/day and still more desirably wherein the substrate material 14 has a WVTR in excess of about 3500 g/m²/day. The breathable material can be formed by any one of various methods known in the art.

In certain embodiments, the substrate material 14 comprises one or more liquid barrier layers having a hydrohead of at least about 50 mbar and, optionally, the liquid barrier has a hydrohead value greater than about 80 mbar and optionally greater than about 150 mbar.

In certain embodiments, at least one layer of breathable material comprises a stretched filled-film that includes a thermoplastic polymer and filler. These (and other) components can be mixed together, heated and then extruded into a monolayer or multilayer film. The filled film may be made by any one of a variety of film forming processes known in the art such as, for example, by using either cast or blown film equipment. In certain embodiments, two or more layers of article 10 are simultaneously made such as, for example, by co-extrusion. As an example, methods of forming multilayer films are disclosed in U.S. Pat. Nos. 4,522,203; 4,734,324 and commonly assigned U.S. Pat. No. 6,075,179 to McCormack et al. and U.S. Pat. No. 6,045,900 to Haffner et al.; each of which patent documents is herein incorporated by reference.

An exemplary stretched filled-film comprises a stretched microporous filled-film. Such films are typically filled with particles or other matter and then crushed or stretched to form a fine pore network throughout the film. The fine pore network allows gas and water vapor to pass through the film while acting as a barrier to liquids and particulate matter. The amount of filler within the film and the degree of stretching are controlled so as to create a network of micropores of a size and frequency to impart the desired level of breathability to the fabric. By way of example only, exemplary microporous films are described in U.S. Pat. No. 5,855,999 to McCormack et al.; U.S. Pat. No. 5,695,868 to McCormack; U.S. Pat. No. 5,800,758 to Topolkaraev et al.; U.S. Pat. No. 6,075,179 to McCormack et al.; U.S. Pat. No. 6,909,028 to Shawver et al.; U.S. Pat. No. 4,777,073 to Sheth; and U.S. Pat. No. 4,867,881 to Kinzer; each of which patent documents is herein incorporated by reference.

Thermoplastic polymers suitable for use in the fabrication of stretched microporous filled-films of the present invention include, but are not limited to, polyolefins including homopolymers, copolymers, terpolymers and blends thereof. In this regard, amorphous polyolefin and/or "polyolefin based" films are also believed suitable for use in the present invention. For purposes of the present invention a polymer is considered to be "polyolefin-based" if olefin polymers comprise greater than 50 weight percent of the polymeric portion of the film, exclusive of any filler materials. Additional film forming polymers which may be suitable for use with the present invention, alone or in combination with other polymers, include ethylene vinyl acetate (EVA), ethylene ethyl acrylate (EEA), ethylene acrylic acid (EAA), ethylene methyl acrylate (EMA), ethylene normal butyl acrylate (EnBA), polyester, polyethylene terephthalate (PET), nylon, ethylene vinyl alcohol (EVOH), polystyrene (PS), polyurethane (PU), polybutylene (PB), and polybutylene terephthalate (PBT), cellophane, polylactide (PLA), and polyhydroxybutyrate (PHB). However, polyolefin polymers are preferred such as, for example, polymers of ethylene and propylene as well as copolymers, terpolymers and blends thereof; examples include, but are not limited to, linear low density polyethylene (LLDPE) and ethylene-propylene copolymer blends.

As indicated above, breathable stretched filled-films can include filler to impart microporosity to the film upon stretching. As used herein, a "filler" is meant to include particulate and/or other forms of materials which can be added to the film polymer extrusion blend which will not chemically interfere with or adversely affect the extruded film and further which can be substantially uniformly dispersed throughout the film. Generally the fillers will be in particulate form with average particle sizes in the range of about 0.1 to about 10 microns, and desirably from about 0.1 to about 4 microns. As used herein the term "particle size" describes the largest dimension or length of the filler. Both organic and inorganic fillers are contemplated for use with the present invention provided they do not interfere with the film forming process and subsequent embossing or laminating processes. Examples of fillers include, but are not limited to, calcium carbonate ($CaCO_3$), various clays, silica ($SiO_2$), alumina, barium sulfate, talc, sodium bicarbonate, magnesium sulfate, zeolites, aluminum sulfate, cellulose-type powders, diatomaceous earth, gypsum, magnesium sulfate, magnesium carbonate, polyphosphate, barium carbonate, kaolin, mica, carbon, magnesium oxide, aluminum hydroxide, pulp powder, wood powder, cellulose derivatives, polymeric particles, chitin and chitin derivatives and the like. The filler particles may optionally be coated with a fatty acid, such as stearic acid or behenic acid, and/or other material in order to facilitate the free flow of the particles (in bulk) and their ease of dispersion into the polymer. The microporous filled-films desirably comprise from about 20% to about 40% filler by volume and more desirably comprise between about 30% and about 40% filler by volume. As a particular example, a filled-film using a calcium carbonate particles, or a filler with a similar density to that of calcium carbonate, desirably contains at least about 35% by weight filler (based upon the total weight of the filled-film), and more desirably from about 45% to about 70% by weight filler.

The stretched filled-films that have been stretched to create a network of micropores, rendering the film breathable, are typically stretched to the point of "stress-whitening". Thus, since the network of micropores created by the separation of the polymeric matrix from the filler particles creates a white, opaque film, the use of such fillers alone can impart a white appearance to the film. Optionally, coloring agents such as dyes and/or pigments can be used in addition to filler to create breathable microporous films having a variety of colors. Suitable coloring agents include both organic and/or inorganic pigments and dyes. In certain embodiments, the coloring agents are used in amount less than about 2.0% by weight (based upon the polymeric portion of the film), optionally between about 0.01% and about 0.5% by weight (based upon the polymeric portion of the film). Pigments and/or dyes can be added to the film by means known in the art. In this regard, pigments are optionally added by pre-compounding the pigment with the desired resin to form a resin concentrate with a relatively high percent of pigment and then blending a selected amount of the resin concentrate with unpigmented resin during processing to form a matrix having the desired pigmentation levels. Opacifying agents, an example being titanium dioxide, can optionally be used in the first layer in addition to the filler. In certain embodiments, the opacifying agents are present in an amount from about 0% up to about 10% by weight (based on the total weight of the filled-film).

In another embodiment, the above described substrate material 14 of article 10 can optionally be laminated to an additional layer or sheet. In certain embodiments, it may be desirable to laminate flexible material 14 to a sheet material whereby the laminate takes advantage of the strength and integrity of the sheet material as well as the above described properties of the substrate material 14. If incorporated, the additional layer or sheet is optionally on the garment facing surface 18 of substrate material 14. In certain embodiments, the sheet material can comprise a nonwoven web, a foam, a scrim, a woven or knitted fabric and multilayer laminates thereof. In certain other embodiments, the sheet can comprise a low basis weight nonwoven fabric having numerous openings or voids extending through the thickness of the fabric. As an example, the nonwoven fabric can comprise a nonwoven web of spunbond fibers having a basis weight between about 8 g/m$^2$ and about 50 g/m$^2$, optionally, a spunbond fiber web having a basis weight between about 12 g/m$^2$ and about 34 g/m$^2$. Spunbond fiber fabrics and methods for making the same are known in the art and, as examples, spunbond fiber fabrics and processes of making the same are described in U.S. Pat. No. 4,692,618 to Dorschner et al., U.S. Pat. No. 4,340,563 to Appel et al. and U.S. Pat. No. 3,802,817 to Matsuki et al.; and U.S. Pat. No. 5,382,400 to Pike et al. and PCT Publication No. WO98/23804; each of which patent documents are herein incorporated by reference. Generally, methods for making spunbond fiber nonwoven webs include extruding molten thermoplastic polymer through spinnerets and drawing the extruded polymer into fibers, reducing the fiber diameter, and forming a web of randomly arrayed fibers on a collecting surface. Spunbond fiber webs can be made from various polymers and, in a preferred embodiment, the spunbond fibers desirably comprise a polyolefin and still more desirably comprise a propylene polymer. In certain embodiments, pigmented, dyed or otherwise colored nonwoven materials are used.

Depending on the material selected for the substrate material 14, the substrate material 14 may actively attach to the body of the user using electrostatic means; suction means or a body attaching adhesive may be placed on body facing surface 16 of substrate material 14 to attach the article to the body of a user. Electrostatic means can be used by providing or forming the substrate material 14 such that portions of the body facing surface 16 of substrate material 14 comprises a material which has an affinity for the body of a user, causing the substrate material 14 to "cling" to the body of the user. Examples of such materials include ethylene vinyl acetate, low density polyethylene and other similar materials know to those skilled in the art. Alternatively, electrostatic means can be achieved by materials having a multiplicity of miniature spike-type protrusions, a dry, strong, reversible, self-cleaning adhesive that has been referred to as "gecko feet" materials. The feet of a Tokay gecko (Gekko gecko) contain approximately one billion spatulae that appear to provide a sufficiently large surface area in close contact with the substrate for adhesion to be the result of van der Waals forces. "Gecko feet" material are as described in U.S. Pat. No. 7,811,272 to Lindsey et al., filed Dec. 29, 2003, the specific disclosure of which materials is found at col. 3, line 44 to col. 5, line 34 and is herein incorporated by reference. Suction means may be achieved by shaping the body facing surface 16 of substrate material 14 to conform to the body of the user, much like a contact lens fits to the eye. Generally, suction means can be achieved by forming the body facing surface 16 of substrate material 14 into a three-dimensional shape. The easiest way to achieve body attachment is to place a body attaching adhesive or mucosal attaching adhesive on body facing surface 16 of substrate material 14.

Body Attaching Adhesives

The adhesive 20 employed for attachment of the labial adhesive patch 12 is adapted to securely attach the article to body but at the same time enable the user to manually remove the article in a hurt free fashion. In addition, it is critical that a shear force required to separate the adhesive 20 from skin be greater than the force required to deform the substrate material 14. This property can be represented as follows:

$F_s > F_m > F_p$; where
$F_s$=Shear Force Required to Separate the Adhesive from Skin at 0°
$F_m$=Force Required to Deform the Substrate Material
$F_p$=Peel Force of Adhesive at 30°

By insuring that the adhesive 20 possesses the above described adhesive property the article 10 will remain securely in place during use while at the same time enabling the substrate 14 to move with the body. The adhesive 20 also preferably possesses the ability to stick to skin, mucosa and preferably retains its adhesive properties in moist conditions. In addition the adhesive preferably provides the above described properties while at the same time permits the article to be selectively removed from the body in a hurt-free manner.

The adhesive 20 may be of any kind, e.g. an acrylic adhesive, a hydrogel adhesive or a hydrocolloid adhesive, provided that the adhesive functions in the manner described above. The adhesive 20 may comprise synthetic homo-, co- or block-copolymers, polyacrylate and copolymerisates thereof, polyurethane, silicone, polyisobutylene, polyvinyl ether and natural or synthetic resins or mixtures thereof. The adhesive may suitably be of the type disclosed in U.S. Pat. Nos. 4,231,369, 4,367,732, 4,867,748, and 5,714,225, herein incorporated by reference.

In one specific embodiment of the invention the adhesive 20 may be any pressure sensitive adhesive, and preferably a hot melt adhesive, that possesses the specific rheological properties set forth in further detail below. The rheological analysis of an adhesive is a method of determining the viscoelastic properties of the adhesive. Rheometer devices for determining rheological properties of adhesives are well known to those skilled in the art. For example, a Rheometrics Solids Analyzer II manufactured by Rheometrics Inc., of Piscataway N.J. is a suitable commercially available device.

In one specific embodiment of the invention, the adhesive 20 preferably has the following properties: (i) a ratio of the Dynamic Shear Storage Modulus (G') measured at 37° C. and 100 radians/s to Dynamic Shear Storage Modulus (G') at 37° C. and 0.1 radians/second that is greater than or equal to 4.5; and (ii) a glass transition temperature Tg between −20° C. and 15° C.

The above described properties can be represented by the following formulas:

$G'_{[100\ rad/sec@37°\ C.]} / G'_{[0.1\ rad/sec@37°\ C.]} \geq 4.5$; and
−20° C.≤Tg (° C.)≤15° C.

In one specific embodiment of the invention, the adhesive 20 preferably has a Tg value of between −20° C. and 15° C., more preferably between −20° C. and 0°, and most preferably between −20° C. and −10° C.

In one specific embodiment of the invention, the adhesive 20 preferably has a $G'_{[100\ rad/sec@37°\ C.]} / G'_{[0.1\ rad/sec@37°\ C.]}$ value of greater than or equal to 4.5, more preferably between 4.5 and 7, and most preferably between 4.8 and 6.

In certain embodiments, the body attaching adhesive 20 has a peel force, when measured by the Peel Test as described below in the Procedure for Measuring Peel Force, of from about 100 to about 700 N/m, optionally from about 100 to about 300 N/m.

In one specific embodiment of the invention, the adhesive 20 preferably has more than about 50% by weight of a liquid plasticizer, preferably more than about 65% by weight of a liquid plasticizer, and most preferably more than about 80% by weight of a liquid plasticizer. Suitable liquid plasticizers may include white oils, mineral oils, paraffinic process oils, polyethylene glycol, glycerin, polypropylene glycol, napthenic oils, and liquid polyterpenes. The liquid plasticizer preferably has a molecular weight of less than 1000 g/mole, more preferably less than 750 g/mole and most preferably less than 500 g/mole.

In one specific embodiment of the invention the adhesive 20 is based upon block copolymers, preferably, those which may include linear or radial co-polymer structures having the formula $(A-B)_x$ wherein block A is a polyvinylarene block, block B is a poly(monoalkenyl) block, x denotes the number of polymeric arms, and wherein x is an integer greater than or equal to one. Suitable block A polyvinylarenes include, but are not limited to Polystyrene, Polyalphamethylstyrene, Polyvinyltoluene, and combinations thereof. Suitable Block B poly(monoalkenyl) blocks include, but are not limited to conjugated diene elastomers such as for example polybutadiene or polyisoprene or most preferably hydrogenated elastomers such as ethylene-butylene or ethylene-propylene or polyisobutylene, or combinations thereof, specifically, adhesives consisting of styrene-ethylene-butylene-styrene (SEBS) block copolymer and mineral oils, paraffinic or napthenic process oils, and optionally a suitable tackifying resins include natural and modified resins; glycerol and pentaerythritol esters of natural and modified resins; polyterpene resins; copolymers and terpolymers of natural terpenes; phenolic modified terpene resins and the hydrogenated derivatives thereof; aliphatic petroleum resins and the hydrogenated derivatives thereof; aromatic petroleum resin and the hydrogenated derivatives thereof; and aliphatic/aromatic petroleum resins and the hydrogenated derivatives thereof, and combinations thereof.

Adhesives of the type described above are commercially available from National Starch and Chemical, Bridgewater, NJ. Specific examples of adhesives particularly useful for the present invention include adhesives identified by product codes 95-2(34-548B) and 85-2 (34-547B) commercially available from National Starch and Chemical, Bridgewater, NJ.

In certain embodiments, the body attaching adhesive is a polysiloxane adhesive as described in U.S. Pat. No. 5,618,281 to Betrabet et al., which patent is herein incorporated by reference.

The adhesive 20 may be positioned on the body-facing surface 16 of substrate material 14 in an open pattern or a closed pattern. An example of an "open" pattern of the adhesive would be to have individual beads of adhesive applied in a discontinuous fashion. "Closed pattern" means the adhesive 20 covers or substantially covers the body-facing surface 16. In certain embodiments, the adhesive 20 extends over a surface area that is about 5% to about 80% of the surface area of the body facing surface 16. In the present invention, the closed pattern can be advantageous since the adhesive 20 may form a seal with the body of the wearer to prevent leaks from the article 10. The adhesive forms a dam which prevents leaks from the entire perimeter of the article 10.

In one embodiment of the present invention, the adhesive 20 may be placed on the entire body-facing surface 16 of substrate material 14. In another alternative embodiment of the present invention, the adhesive 20 may be placed along the outer portions of the body-facing surface 16 near the periphery of substrate material 14, such that no adhesive is near or on the center portion of substrate material 14.

The adhesive 20 may be applied in a pattern of small discrete dots so as to leave numerous areas of body-facing surface 16 free from adhesive. Alternatively, the adhesive may be applied as a continuous bead, or may be applied as a series of semi-continuous beads. Other suitable adhesive patterns may be selected for applying the adhesive 20 to the body-facing surface 16 of the article 10. For example, adhesive patterns can be oval, swirls, various linear or non-linear arrays of adhesive longitudinally, and/or transversely oriented and reticulated webs having unobstructed interstices between the adhesive fibers or combinations thereof. Alternatively, the adhesive 20 may be applied in the form of other suitable patterns as repeating or nonrepeating patterns. In certain embodiments, the above described patterns may be applied to the surface of the article 10 (e.g., on the body facing surface 16) or between layers of article 10. As stated above, the adhesive patterns may be open or closed. The weights of adhesives are limited to less than about 800 $g/m^2$, and generally less than about 400 $g/m^2$. Generally, the weight of the adhesive is at least 20 $g/m^2$. Typically, the adhesive is applied in an amount of about 100 to about 400 $g/m^2$. The limitations on the basis weight of the adhesive are important to provide the correct adhesive characteristics for applying directly to the wearer's vulva region and optionally the pubic and perinea regions of the wearer's body. If the basis weight is too high, the article will have a sticky feeling or otherwise uncomfortable feeling. If the basis weight of the adhesive is too low, there may be insufficient adhesion to the body of the wearer.

Generally, the adhesive 20 is applied in a manner which is symmetrical about the longitudinal extending centerline 11 which bisects the article 10 and divides the article 10 into substantially equal portions. This symmetrical pattern provides the wearer a balanced feel when wearing the article 10. The symmetrical pattern also reduces the perception of any associated discomfort when the article 10 is removed from the body.

Mucosal Attaching Adhesive

Figure 6:
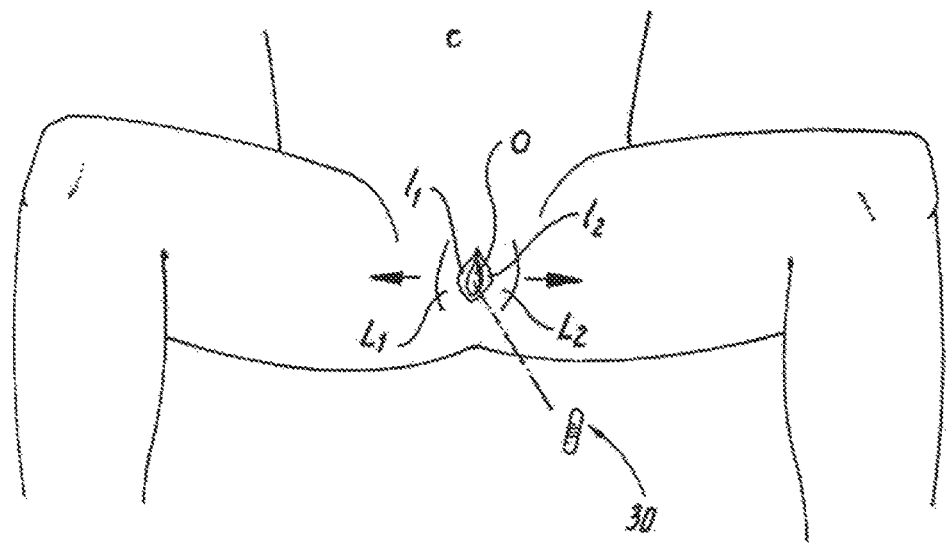
FIG. 6 is a schematic view depicting the manner in which the article is applied to a user's inner labial mucosal region.

In certain embodiments, the adhesive 20 is a mucosal attaching adhesive employed for attachment of the inner labial patch 30 (as shown in FIGS. 6, 7 and 7a) which is adapted to securely attach inner labial patch 30 in the inner labial mucosal region over (i.e., covering) the introitus but at the same time enable the user to manually remove the article in a hurt free fashion. Adhesives suitable for mucosal attachment (or adherence) of inner labial patch 30 to the inner labial mucosal region include non-pressure sensitive adhesive substances, muco- or bioadhesive materials or mixtures thereof. In certain embodiments, the non-pressure sensitive adhesive substance is a substance that has no initial tack at the time of application so that it will not stick to the wrong portions of the wearer's body when the device is placed between the labia where it develops tack. Optionally, the non-pressure sensitive adhesive substance includes moisture-activated substances which become viscous and develop a tack when contacted by relatively small amounts of moisture.

Suitable non-pressure sensitive adhesive substances include (or are selected from the group consisting of) waxes (such as microcrystalline waxes, paraffinic waxes, silicone waxes, polyethylene waxes), fatty alcohols, high molecular weight alcohols, fatty acids, petroleum jelly, sealing ointments, non-ionic surfactants such as ethoxylated alcohols, ethoxylated long chain alcohols, and ethoxylated fatty acids, alkoxylated amide, alkoxylated amines, alkyl amido alkyl amines, alkyl substituted amino acids, sucrose fatty acid esters and mixtures thereof. An example of sucrose fatty acid esters is OLEAN® (olestra) manufactured by the Procter & Gamble Company of Cincinnati, Ohio under U.S. Pat. No. 5,085,884 issued Feb. 4, 1992 and U.S. Pat. No. 5,236,733 issued Aug. 17, 1993, both to Young, et al. and U.S. Pat. No. 5,422,131 issued to Elsen, et al., each of which patents is herein incorporated by reference. Without wishing to be bound by any particular theory, it has been theorized that such materials may hold an object in place due to high viscosity or surface tension.

Suitable muco- or bioadhesive materials include any hydrophilic polymer with strong hydrogen bonding. For most commercial applications it is blends of polymers with hydrophilic/hydrophobic character to ensure smooth dissolution and release properties. In certain embodiments, the muco- or bioadhesive materials are selected from the group consisting of natural, synthetic or biological polymers, lipids, phospholipids and the like and mixtures thereof. Examples of natural and/or synthetic polymers include (or are selected from the group consisting of) cellulosic derivatives (such as methylcellulose, carboxymethyl cellulose, hydroxyethyl cellulose, hydroxyethylmethyl cellulose, hydroxypropyl cellulose [HPC-Methocel] etc.), natural gums (such as guar gum, xanthan gum, locust bean gum, karaya gum, veegum etc), polyacrylates (such as carboxyvinyl polymer [Carbopol], polycarbophil, etc), cyanoacrylates, alginates, polyoxyethylenes, polyethylene glycols (PEG) of all molecular weights (preferably a weight-average molecular weight of between 1000 and 40,000 Da, of any chemistry, linear or branched), dextrans of all molecular weights (preferably a weight-average molecular weight of between 1000 and 40,000 Da of any source), block copolymers, such as those prepared by combinations of lactic and glycolic acid (PLA, PGA, PLGA of various viscosities, molecular weights and lactic-to-glycolic acid ratios), polyethylene glycol-polypropylene glycol block copolymers of any number and combination of repeating units (such as Pluronics, Tektronix, or Genapol block copolymers), combination of the above copolymers either physically or chemically linked units (for example PEG-PLA or PEG-PLGA copolymers), and mixtures thereof. Optionally, the bioadhesive excipient is selected from the group of polyethylene glycols, polyoxyethylenes, polyacrylic acid polymers, such as Carbopols (such as Carbopol 71G, 934P, 971P 974P) and polycarbophils (such as Noveon AA-1, Noveon CA-1, Noveon CA-2), cellulose and its derivatives and most preferably it is polyethylene glycol, carbopol, and/or a cellulosic derivative or a mixtures thereof. Other suitable bioadhesives can be found in U.S. Pat. No. 6,585,997 to Moro et al., the specific disclosure of which is found at col. 8, line 47 to col. 9, line 38 and is herein incorporated by reference; in addition to the foregoing, the remainder of U.S. Pat. No. 6,585,997 is also herein incorporated by reference.

In certain embodiments, the muco- or bioadhesive material used as adhesive 20 is a muco- or bioadhesive composition. In one embodiment, the muco- or bioadhesive composition is a composition comprising: from about 85% to 95% (optionally about 92.5%) of drum dried waxy corn starch (DDWM) e.g. pregelatinized starch 12410, Cerestar; from about 4% to about 10% (optionally 6.2%) Carbopol 974P, BF Goodrich; and from about 0.5% to 2% (optionally 1.3%) Sodium stearyl fumurate, Ludeco. In another embodiment, the muco- or bioadhesive composition is a composition comprising: from about 40% to about 50% (optionally 47%) polyvinylpyrrolidone (PVP) K 90, ISP Technologies; from about 10% to about 20% (optionally 16%) hydroxypropyl cellulose, Klucel HK Pharm; and from about 30% to about 40% (optionally 37%) Propylene glycol.

In certain embodiments, the muco- or bioadhesive material is a silicone gel adhesive. Silicone gel adhesives are known in the art. As detailed in WO 2008/057155, they are lightly crosslinked silicone polymers that have a viscoelastic, jelly-like consistency. They are typically formed using a hydrosilation reaction between an alpha-omega vinyl terminated polydimethyl siloxane and a Si—H containing siloxane catalyzed by a platinum catalyst. Further details on their formulation and properties are disclosed, for example, in U.S. Pat. Nos. 4,991,574 and 5,145,933 and US Pat. Pub. US20070202245, each of which patent documents is herein incorporated by reference.

In certain embodiments, the silicone gel adhesive is incorporated as silicone gel adhesive precursors. Suitable silicone gel adhesive precursors are commercially available. Several manufacturers sell versions of these materials based on platinum catalyzed two component addition cure chemistry. Such materials (uncured) typically have viscosities of about 200 mPa·s to about 6000 mPa·s as measured by ASTM D1084B. Examples of suitable commercially available silicone gel adhesive precursors useful in certain embodiments of the present invention include Blue Star Silicones Silbione™ RT Gel 4317, Dow Corning's MG 7-9800 Soft Skin Adhesive (SSA) (viscosity of each of part A and part B of 400 mPa s as measured by ASTM D1084B) and MG 7-9850 Soft Skin Adhesive (SSA) (viscosity of each of part A and part B of 2900 mPa s as measured by ASTM D1084B), and Wacker SilGel™ 612, all of which are two component 100% solids platinum catalyzed addition-cure materials. In one embodiment of the present invention, the silicone gel adhesive precursors used have (in its uncured state) a viscosity for each of part A and part B of from about 200 mPa·s to about 600 mPa s, or optionally from about 300 mPa·s to about 500 mPa s as measured by ASTM D1084B. In another embodiment, the silicone gel adhesive precursors used have (in its uncured state) a viscosity for each of part A and part B of from about 1500 mPa s to about 6000 mPa s or optionally from about 2500 mPa·s to about 4000 mPa s as measured by ASTM D1084B.

In certain embodiments, the coating weight of the silicone gel adhesive typically ranges from about 20 $g/m^2$ to about 150 $g/m^2$ (preferably, from about 40 $g/m^2$ to about 120 $g/m^2$). The silicone gel adhesive coating is typically from about 0.8 to about 6 mils thick. Lower coating weights may not provide adequate adhesion properties to mucosa.

In certain embodiments, the silicone gel adhesive in the form of the silicone gel adhesive precursors, as described above, is used as the body attaching adhesive of the labial adhesive patch 12.

In certain embodiments, the adhesive, whether body attaching adhesive or a mucosal attaching adhesive, is a mixture of adhesive (i.e., body attaching or mucosal attaching) and particles of absorbent material. Examples of suitable absorbent materials include, but are not limited to, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. The mixture of adhesive and particles of absorbent material must be formed and/or incorporated on either labial adhesive patch 12 or inner labial patch 30 such that patches 12 and 30 remain substantially non-absorbent.

Test Methods:

Unless otherwise specified, all measurements are conducted at a temperature of 22° C.-25° C. and a relative humidity of 50±5%. The methods are performed on the article in state (or condition) in which it is worn by the user (i.e., without a release liner or any other structural aid).

Procedure for Measuring Peel Force:

The peel force of the body attaching adhesive is measured by the following Peel Test.

The peel force of the body attaching adhesive is measured using the ASTM D6862 peel testing procedure as modified below. The test product is adhered to a plate made of nylon 6,6 for testing. The plate material is available from Mcmaster Carr inc, part #8733K41. Prior to testing, the test surface of the plate is imparted with a rough texture on a milling machine by machining at 400 rpm and 40 inch/minute feed rate with a SandvikRA-390-076R25-11 m shell mill and corokeyR390-11-08M-PM 1030 carbide inserts. A 50% isopropyl alcohol and water cleaning mixture with a lint free cloth is used to clean the surface of the plate before testing.

Strips of the article of up to 1 inch wide and at least 1 inch in length are provided as the test product(s). The adhesive surfaces of the test product is positioned to contact the roughened nylon surface of the plate so that the length of the test product is perpendicular to the longitudinal edge of the plate and at least ½ inch of test product extends off the plate to start the peel test. A 2 lb. rubber roller is rolled over the surfaces to insure consistent adhesion.

The nylon plate is affixed to a testing sled which is mounted in the lower jaw of an Instron machine (Model #1122). The testing sled is designed to hold the nylon plate at a constant 30 degree angle relative to the peeling direction during peeling. The Instron machine is adjusted so that the unaffixed end of the test product (i.e, the end opposite the end of the test product contacting the nylon plate) is held in the upper jaw of the Instron machine.

The upper and lower jaws of the Instron machine are separated at a rate of 1 inch/minute, forcing the test product to peel from the nylon plate. An approximately constant peel force is recorded by the Instron as a plot of peel force as a function of peel distance. Peel force for the test product is an average force over the horizontal section of the plotted curves beginning at the point on the plot where stable peeling occurs to the point where the test product is close to complete detachment from the plate (and the force begins to drop rapidly). The average peel force is divided by the width of the test products and reported in units of Newtons per meter as the peel force of the test product.

The above procedure is repeated at least two times for a total of at least 3 test products tested. The average peel force of the at least 3 test products tested is calculated and reported.

Procedure for Measuring Tensile Stretchability

The Tensile Stretchability of the articles of the present invention is measured by the following procedure. Prior to performing the tensile stretchability test, the adhesive surface should be detackified by a light coating of talcum powder or similar material (such as corn starch).

The tensile stretchability is measured by ASTM test method D882 as modified below:

A strip of the article used as the test product is cut to a width between 0.25 to 1.0 inches and a length of 2.5 inches. The test product is placed between the jaws of an Instron machine (model #1122) so that there is no slack and the jaws are separated by 2.0 inches. The initial jaw separation is referred to as the gauge length and can be adjusted to accommodate different sample sizes. The jaws are separated at a rate of 10 times the gauge length per minute. For example, a 2 inch gauge length requires a rate of 20 inches per minute or a 1 inch gauge length requires a rate of 10 inches per minute. The force applied to stretch the test product to 120% of the gauge length is measured and recorded.

This measurement is the applied force for a 20% extension.

The applied force for a 20% extension is divided by the width of the test product to give stretchability in terms of Newtons per meter.

The above procedure is repeated at least two times for a total of at least 3 test products tested. The average applied force for a 20% extension (in Newton per meter) of the at least 3 test products tested is calculated and reported.

Procedure for Measuring Absorbent Capacity As noted above, articles of the present invention are "non-absorbent" or "substantially non-absorbent." "Substantially non-absorbent" as used herein means the article has a total absorbent capacity of less than about 0.3 g, more preferably less than about 0.1 g, and more preferably less than about 0.05 g. A procedure is provided below for measuring the average total absorbent capacity of the articles of the present invention.

At least three new article samples are required as test specimens to conduct the average absorbent capacity test described below. The average absorbent capacity test is conducted on 20.0 mm×20.0 mm square test specimen cut from the portion of the article adapted to be placed over the vaginal opening. Prior to doing the test, a stack of clean, dry, filter papers are prepared for every test specimen. The filter paper is Whatman No. 4 Qualitative Circles (150 mm diameter) or equivalent. Five filter paper circles are stacked neatly together and placed near the area where the test specimen will be submerged.

The weight of each of the three dry 20.0 mm×20.0 mm test specimens is measured before beginning the test. A 20.0 mm×20.0 mm test specimen is submerged in a saline solution (0.9%) for 15 minutes. Upon removal from the saline solution, the test specimen is laid on the stack of dry Whatman filter paper to make full contact between the specimen surface and the filter paper surface. Once full contact occurs, the test specimen is immediately lifted and flipped 180 degrees so that the side facing away from the filter paper now comes in full contact with a clean area of the filter paper. Once full contact occurs, the test specimen is immediately lifted. After both sides of the specimen have made contact with dry areas of the filter paper, it is then hung so that saline can freely drip for 12 minutes. The wet weight of test specimen are then measured to the nearest one hundredth of a gram. The dry weight of the test specimen is then subtracted to determine the absorbent capacity of the test specimen. This is repeated for three 20.0 mm×20.0 mm test specimens and the absorbent capacity average is taken to provide the average total absorbent capacity of the article.

As described above, the article according to the present invention is structured and arranged to cover the vaginal opening during use. Unlike prior art devices that function by means of absorbing fluid, the article according to the present invention is "substantially non-absorbent". Since the article according to the present invention does not function by means of absorption, but rather functions by means of maintaining menstrual fluid within the body, the shortcomings of prior art articles such as sanitary napkins, liners, tampons and the like are avoided.

Although the article 10 according to the present invention described above has been described in the context of maintaining menstrual fluid within the vagina the article 10 could be employed to maintain any vaginal exudate within the body. "Vaginal exudate" as used herein means any body fluid, tissue, or other substance that could be released via the vagina including, but not limited to menstrual fluid, vaginal discharge (including cervical mucus, epithelial cells), vaginal treatments and medications, and semen.

Procedure for Measuring Fluid Penetration Time.

The method for determining the Fluid Penetration Time (FPT) for articles of the present invention is provided below. Three new article samples are required to conduct Fluid Penetration Time (FPT) test described below.

Fluid Penetration Time is measured by placing an article sample to be tested under a Fluid Penetration Test orifice plate. The orifice plate consists of a 7.6 cm×25.4 cm plate of 1.3 cm thick polycarbonate with an elliptical orifice in its center. The elliptical orifice measures 3.8 cm along its major axis and 1.9 cm along its minor axis. The orifice plate is arranged on the article sample to be tested at a corresponding location on the article sample. The longitudinal axis of the elliptical orifice is arranged parallel to the longitudinal axis of the article sample to be tested.

Test fluid is made of the following mixture to simulate bodily fluids: 49.5% of 0.9% sodium chloride solution (VWR catalog #VW 3257-7), 49.05% Glycerin (Emery 917), 1% Phenoxyethanol (Clariant Corporation Phenoxetol™) and 0.45% Sodium Chloride (Baker sodium chloride crystal #9624-05).

A graduated 10 cc syringe containing 1 ml of test fluid is held over the orifice plate such that the exit of the syringe is approximately 3 inches above the orifice. The syringe is held horizontally, parallel to the surface of the test plate. The fluid is then expelled from the syringe at a rate that allows the fluid to flow in a stream vertical to the test plate into the orifice and a stop watch is started when the fluid first touches the sample to be tested. The stop watch is stopped when a portion of the surface of the sample first becomes visible above the remaining fluid within the orifice. The elapsed time on the stop watch is the Fluid Penetration Time. The average Fluid Penetration Time (FPT) is calculated from taking the average of the three article samples.

Optional Components

Articles according to the present invention may further include any number of features commonly found in conventional sanitary protection articles. In certain embodiments, the optional components are applied on either one side or both sides of the article 10. For example (and without being limited to the specific enunciated examples), articles according to the present invention may include odor control additives, color cues, fragrances, skin care composition such as moisturizers, lubricants, temperature change agents, antibacterial and antifungal agents, pH control additives, prebiotics/probiotics and other actives such as estrogen and/or progestin, colored and/or printed layers, one or more embossed layers, other skin soothing additives, packaging enhancements (e.g. tri-fold type packaging or dispensers), finger lift enhancements for the release paper, placement indicators, and any number of other features known to those of skill in the sanitary protection arts.

In certain embodiments, the optional components (such as the odor control additives, color cues, fragrances, skin care composition such as moisturizers, lubricants, temperature change agents, antibacterial and antifungal agents, pH control additives, prebiotics/probiotics and other actives such as estrogen and/or progestin) are suitably encapsulated, and may, in some embodiments, be microencapsulated, to inhibit activation (or release) of such components until placement of the article 10 on the user is undertaken. For example, the temperature change agent (described in more detail below) may be encapsulated and located adjacent an activating agent, such as water in some instances, such that upon rupturing the capsule (or microcapsule) such as by pinching or squeezing the article 10 at the location of the encapsulated temperature change agents in or on the article 10, the activating agent combines with the temperature change agent to induce a temperature change sensation.

Odor Control Agents

Concerning odor control, perfumes and/or odor control additives are optionally added. Suitable odor control additives are all substances of reducing human (or mammalian) bodily odors or odors associated or human (or mammalian bodily fluids) as known in the art. Thus, suitable odor control additives are inorganic materials, such as zeolites, activated carbon, bentonite, silica, aerosile, kieselguhr, clay; chelants such as ethylenediamine tetraacetic acid (EDTA), cyclodextrins, aminopolycarbonic acids, ethylenediamine tetramethylene phosphonic acid, aminophosphate, polyfunctional aromates, N,N-disuccinic acid, polyphosphates. Mixtures of any of the above may also be used.

Suitable odor control additives further include antimicrobial and antifungal agents. Nonlimiting examples of antimicrobial and antifungal actives include b-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentarnidine, gentamicin, kanamycin, lineomycin, methacycline, methenamine, minocycline, neomycin, netilmicin, paromomycin, streptomycin, tobramycin, miconazole, and tetracycline hydrochloride, erythromycin, zinc erythromycin, erythromycin estolate, erythromycin stearate, amikacin sulfate, doxycycline hydrochloride, capreomycin sulfate, benzalkonium chloride; benzethonium chloride; benzoic acid and its salts; cetylpyridinium chloride; triclosan; triclocarban; as well as surfactants having an HLB value of less than 12. Mixtures of any of the above can also be used.

Suitable odor control additives are further compounds with anhydride groups such as maleic-, itaconic-, polymaleic- or polyitaconic anhydride, copolymers of maleic acid with $C_2$-$C_8$ olefins or styrene, polymaleic anhydride or copolymers of maleic anhydride with isobutene, di-isobutene or styrene, compounds with acid groups such as ascorbic, benzoic, citric, salicylic or sorbic acid and fluid-soluble polymers of monomers with acid groups, homo- or co-polymers of $C_3$-$C_5$ mono-unsaturated carboxylic acids. Mixtures of any of the above may also be used.

Suitable odor control additives are further perfumes such as allyl caproate, allyl cyclohexane-acetate, allyl cyclohexanepropionate, allyl heptanoate, amyl acetate, amyl propionate, anethol, anixic aldehyde, anisole, benzaldehyde, benzyl acetete, benzyl acetone, benzyl alcohole, benzyl butyrate, benzyl formate, camphene, camphor gum, laevo-carveol, cinnamyl formate, cis-jasmone, citral, citronellol and its derivatives, cuminic alcohol and its derivatives, cyclal C, dimethyl benzyl carbinol and its derivatives, dimethyl octanol and its derivatives, eucalyptol, geranyl derivatives, lavandulyl acetete, ligustral, d-limonene, linalool, linalyl derivatives, menthone and its derivatives, myrcene and its derivatives, neral, nerol, p-cresol, p-cymene, orange terpenes, alpha-ponene, 4-terpineol, thymol, etc. Mixtures of any of the above may also be used.

In certain embodiments, masking agents are also used as odor control additives. Masking agents are in solid wall material encapsulated perfumes. Optionally, the wall material comprises a fluid-soluble cellular matrix which is used for time-delay release of the perfume ingredient.

In certain embodiments, the suitable odor control additives are transition metals such as Cu, Ag, and Zn, enzymes such as urease-inhibitors, starch, pH buffering material, chitin, green tea plant extracts, ion exchange resin, carbonate, bicarbonate, phosphate, sulfate or mixtures thereof.

In certain embodiments, the odor control additives are plant extracts such as green tea plant extracts, silica, zeolite, carbon, starch, chelating agent, pH buffering material, chitin, kieselguhr, clay, ion exchange resin, carbonate, bicarbonate, phosphate, sulfate, masking agent or mixtures thereof. Suitable concentrations of odor control additives are from 0.5 to 300 gsm.

Skin Care Compositions

Concerning skin care compositions, the articles of the present invention optionally contain a composition which provides either a protective, nonocclusive function (e.g., a relatively liquid impervious but vapor pervious barrier) to avoid skin hyperhydration and skin exposure to materials contained in body exudates, or which delivers, either directly or indirectly, skin care benefits. The composition may be in a variety of forms, including, but not limited to, emulsions, lotions, creams, ointments, salves, powders, suspensions, encapsulations, gels, and the like.

As used herein, the term "effective amount of a skin care composition" refers to an amount of a particular composition which, when applied or migrated to one or more of portions of body-facing surface 16 of substrate material 14 of article 10, will be effective in providing a protective barrier and/or delivering a skin care benefit when delivered via article 10 upon application or over a period of time during. Of course, the effective amount of composition applied to the article will depend, to a large extent, on the particular composition used. Nonetheless, the quantity of the composition on at least a portion of the body-facing surface 16 of substrate material 14 will range from about 0.05 mg/m$^2$ (0.0078 mg/cm$^2$) to about 80 mg/m$^2$ (12 mg/cm$^2$), optionally from about 1 mg/m$^2$ (0.16 mg/cm$^2$) to about 40 mg/m$^2$ (6 mg/cm$^2$), or optionally from about 4 mg/m$^2$ (0.6 mg/cm$^2$) to about 26 mg/m$^2$ (4 mg/cm$^2$). These ranges are by way of illustration only and the skilled artisan will recognize that the nature of the composition will dictate the level that must be applied to achieve the desired skin benefits, and that such levels are ascertainable by routine experimentation in light of the present disclosure.

It will be recognized that of the numerous materials useful in the skin care compositions delivered to skin in accordance with the articles of the present invention, those that have been deemed safe and effective skin care agents are logical materials for use herein. Such materials include Category I actives as defined by the U.S. Federal Food and Drug Administration's (FDA) Tentative Final Monograph on Skin Protectant Drug Products for Over-the-Counter Human Use (21 C.F.R. § 347), which presently include: alantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Other potentially useful materials are Category III actives as defined by the U.S. Federal Food and Drug Administration's Tentative Final Monograph on Skin Protectant Drug Products for Over-the-Counter Human Use (21 C.F.R. § 347), which presently include: live yeast cell derivatives, aldioxa, aluminum acetate, microporous cellulose, cholecalciferol, colloidal oatmeal, cysteine hydrochloride, dexpanthanol, Peruvean balsam oil, protein hydrolysates, racemic methionine, sodium bicarbonate, Vitamin A, and the like.

Many of the FDA monographed skin care ingredients are currently utilized in commercially available skin care products, such as A and D® Ointment, Vaseline® Petroleum Jelly, Desitin® Diaper Rash Ointment and Daily Care® ointment, Gold Bond® Medicated Baby Powder, Aquaphor® Healing Ointment, Baby Magic® Baby Lotion, Johnson's Ultra Sensitive® Baby Cream. These commercial products may be applied to article 10 to create treated articles of the present invention.

As will be discussed hereinafter, the skin care compositions useful in the methods of the present invention preferably, though not necessarily, have a melting profile such that they are relatively immobile and localized on the body-facing surface 16 of substrate material 14 of article 10 at room temperature, are readily transferable to the user at body temperature, and yet are not completely liquid under extreme storage conditions. In certain embodiments, the compositions are easily transferable to the skin by way of normal contact, user motion, and/or body heat.

In certain embodiments, the skin care compositions useful herein are solid, or more often semi-solid, at 20° C., i.e. at ambient temperatures. By "semisolid" is meant that the composition has a rheology typical of pseudoplastic or plastic liquids. When no shear is applied, the compositions can have the appearance of a semi-solid but can be made to flow as the shear rate is increased. This is due to the fact that, while the composition contains primarily solid components, it also includes some minor liquid components. By being solid or semisolid at ambient temperatures, preferred compositions do not have a tendency to flow and migrate to a significant degree to undesired locations of the article to which they are applied. This means less skin care composition is required for imparting desirable therapeutic, protective and/or conditioning benefits.

To enhance immobility of the skin care compositions, the viscosity of the formulated compositions should be as high as possible to prevent flow within the article to undesired location. Unfortunately, in some instances, higher viscosities may inhibit transfer of composition to the user's skin. Therefore, a balance should be achieved so the viscosities are high enough to keep the compositions localized on the surface of the article, but not so high as to impede transfer to the user's skin. Suitable viscosities for the compositions will typically range from about 5 to about 500 centipoise, preferably from about 5 to about 300 centipoise, more preferably from about 5 to about 100 centipoise, measured at 60° C. using a rotational viscometer (a suitable viscometer is available from Lab Line Instruments, Inc. of Melrose Park, Ill. as Model 4537). The viscometer is operated at 60 rpm using a number 2 spindle.

For compositions designed to provide a therapeutic and/or skin protective benefit, a useful active ingredient in these compositions is one or more skin protectants or emollients. As used herein, the term "emollient" is a material that protects against wetness or irritation, softens, soothes, supples, coats, lubricates, moisturizes, protects and/or cleanses the skin. (It will be recognized that several of the monographed actives listed above are "emollients", as that term is used herein.) In certain embodiments, these emollients will have either a plastic or liquid consistency at ambient temperatures, i.e., 20° C. Representative emollients useful in the present invention include, but are not limited to, emollients that are petroleum-based; sucrose ester fatty acids; polyethylene glycol and derivatives thereof; humectants; fatty acid ester type; alkyl ethoxylate type; fatty acid ester ethoxylates; fatty alcohol type; polysiloxane type; propylene glycol and derivatives thereof; glycerine and derivatives thereof, including glyceride, acetoglycerides, and ethoxylated glycerides of $C_{12}$-$C_{28}$ fatty acids; triethylene glycol and derivatives thereof; spermaceti or other waxes; fatty acids; fatty alcohol ethers, particularly those having from 12 to 28 carbon atoms in their fatty chain, such as stearic acid; propoxylated fatty alcohols; other fatty esters of polyhydroxy alcohols; lanolin and its derivatives; kaolin and its derivatives; any of the monographed skin care agents listed above; or mixtures of these emollients. Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are particularly preferred emollients for compositions of the present invention. Suitable fatty acid ester type emollients include those derived from $C_{12}$-$C_{28}$ fatty acids, preferably $C_{16}$-$C_{22}$ saturated fatty acids, and short chain ($C_1$-$C_8$, preferably $C_1$-$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols ($C_{12}$-$C_{28}$, preferably $C_{12}$-$C_{16}$) and shorter chain fatty acids e.g., lactic acid, such as lauryl lactate and cetyl lactate.

Suitable alkyl ethoxylate type emollients include $C_{12}$-$C_{22}$ fatty alcohol ethoxylates having an average degree of ethoxylation of from about 2 to about 30. In certain embodiments, the fatty alcohol ethoxylate emollient is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) and steareth-10 (a stearyl alcohol ethoxylate having an average degree of ethoxylation of 10). When employed, these alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1:4.

Suitable fatty alcohol type emollients include $C_{12}$-$C_{22}$ fatty alcohols, preferably $C_{16}$-$C_{18}$ fatty alcohols. Representative examples include cetyl alcohol and stearyl alcohol, and mixtures thereof. When employed, these fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Other suitable types of emollients for use herein include polysiloxane compounds. In general, suitable polysiloxane materials for use in the present invention include those having monomeric siloxane units of the following structure:

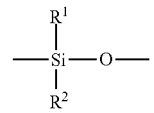

wherein, $R^1$ and $R^2$, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. $R^1$ and $R^2$ radicals of any particular monomeric unit may differ from the corresponding functionalities of the next adjoining monomeric unit. Additionally, the polysiloxane can be either a straight chain, a branched chain or have a cyclic structure. The radicals $R^1$ and $R^2$ can additionally independently be other silaceous functionalities such as, but not limited to siloxanes, polysiloxanes, silanes, and polysilanes. The radicals $R^1$ and $R^2$ may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like. Exemplary aralkyl radicals are benzyl, alpha-phenylethyl, beta-phenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Viscosity of polysiloxanes useful may vary as widely as the viscosity of polysiloxanes in general vary, so long as the polysiloxane is flowable or can be made to be flowable for application to the article 10. This includes, but is not limited to, viscosity as low as 5 centistokes (at 37° C. as measured by a glass viscometer) to about 20,000,000 centistokes. In certain embodiments, the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the article 10 by such methods as, for example, emulsifying the polysiloxane in surfactant or providing the polysiloxane in solution with the aid of a solvent, such as hexane, listed for exemplary purposes only.

Suitable polysiloxane compounds for use in the present invention are disclosed in U.S. Pat. No. 5,059,282 (Ampulski et al), issued Oct. 22, 1991, which patent is herein incorporated by reference. Suitable polysiloxane compounds for use as emollients in the compositions of the present invention include phenyl-functional polymethylsiloxane compounds (e.g., Dow Corning 556 Cosmetic-Grade Fluid: polyphenylmethylsiloxane) and cetyl or stearyl functionalized dimethicones such as Dow 2502 and Dow 2503 polysiloxane liquids, respectively. In addition to such substitution with phenyl-functional or alkyl groups, effective substitution may be made with amino, carboxyl, hydroxyl, ether, polyether, aldehyde, ketone, amide, ester, and thiol groups. In certain embodiments, the substituent groups are selected from the family of groups comprising phenyl, amino, alkyl, carboxyl, and hydroxyl groups. In other embodiments, the substituent group is a phenyl-functional group.

Suitable humectants include glycerine, propylene glycol, sorbitol, trihydroxy stearin, and the like.

When present, the amount of emollient that can be included in the skin care composition will depend on a variety of factors, including the particular emollient involved, the skin benefits desired, the other components in the composition and like factors. The composition will comprise from 0 to about 100%, by total weight, of the emollient. In certain embodiments, the composition will comprise from about 10 to about 95%, optionally, from about 20 to about 80%, or optionally from about 40 to about 75%, by weight, of the emollient.

Another optional component of the skin therapeutic/skin protective compositions of the articles of the present invention is an agent capable of immobilizing the composition (including for example, the emollient and/or other skin condition/protective agents) in the desired location in or on the treated article.

Immobilizing agents useful herein can be selected from any of a number of agents, so long as the properties of the skin care composition provide the skin benefits described herein. In certain embodiments, immobilizing agents will comprise a member selected from the group consisting of $C_{14}$-$C_{22}$ fatty alcohols, $C_{12}$-$C_{22}$ fatty acids, and $C_{12}$-$C_{22}$ fatty alcohol ethoxylates having an average degree of ethoxylation ranging from 2 to about 30, and mixtures thereof. Suitable mobilizing agents include $C_{16}$-$C_{18}$ fatty alcohols, most preferably crystalline high melting materials selected from the group consisting of cetyl alcohol, stearyl alcohol, behenyl alcohol, and mixtures thereof (The linear structure of these materials can speed up solidification on the treated article 10.) Mixtures of cetyl alcohol and stearyl alcohol are particularly preferred. Other preferred immobilizing agents include $C_{16}$-$C_{18}$ fatty acids, most preferably selected from the group consisting of palmitic acid, stearic acid, and mixtures thereof. Mixtures of palmitic acid and stearic acid are particularly preferred. Still other suitable immobilizing agents include $C_{16}$-$C_{18}$ fatty alcohol ethoxylates having an average degree of ethoxylation ranging from about 5 to about 20. Preferably, the fatty alcohols, fatty acids and fatty alcohols are linear.

Other types of immobilizing agents that may be used herein include polyhydroxy fatty acid esters, polyhydroxy fatty acid amides, and mixtures thereof. In certain embodiments, the esters and amides will have three or more free hydroxy groups on the polyhydroxy moiety and are typically nonionic in character. Because of the possible skin sensitivity of those using the articles comprising the skin care composition, these esters and amides should be relatively mild and non-irritating to the skin of such users.

Suitable polyhydroxy fatty acid esters for use in or on the present invention will have the formula:

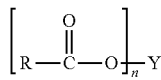

wherein R is a $C_5$-$C_{31}$ hydrocarbyl group, optionally a straight chain $C_7$-$C_{19}$ alkyl or alkenyl, optionally a straight chain $C_9$-$C_{17}$ alkyl or alkenyl, or optionally a straight chain $C_{11}$-$C_{17}$ alkyl or alkenyl, or mixture thereof; Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use in or on the present invention comprises certain sorbitan esters, optionally the sorbitan esters of $C_{16}$-$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates. In certain embodiments, the sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and di-esters are usually the predominant species in these mixtures.

Another class of suitable polyhydroxy fatty acid esters for use in or on the present invention comprises certain glyceryl monoesters, optionally glyceryl monoesters of $C_{16}$-$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use in or on the present invention comprise certain sucrose fatty acid esters, preferably the $C_{12}$-$C_{22}$ saturated fatty acid esters of sucrose. In certain embodiments, the sucrose fatty acid esters are sucrose monoesters and diesters and include sucrose mono- and di-stearate and sucrose mono- and di-laurate.

Suitable polyhydroxy fatty acid amides for use in the present invention will have the formula:

wherein $R^1$ is H, $C_1$-$C_4$ hydrocarbyl, 2-hydroxyethyl, 2-hydroxypropyl, methoxyethyl, methoxypropyl or a mixture thereof, preferably $C_1$-$C_4$ alkyl, methoxyethyl or methoxypropyl, more preferably $C_1$ or $C_2$ alkyl or methoxypropyl, most preferably $C_1$ alkyl (i.e., methyl) or methoxypropyl; and $R^2$ is a $C_5$-$C_{31}$ hydrocarbyl group, preferably straight chain $C_7$-$C_{19}$ alkyl or alkenyl, more preferably straight chain $C_9$-$C_{17}$ alkyl or alkenyl, most preferably straight chain $C_{11}$-$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174,927 (Honsa), issued Dec. 29, 1992 (herein incorporated by reference) which discloses these polyhydroxy fatty acid amides, as well as their preparation.

In certain embodiments, the Z moiety will be derived from a reducing sugar in a reductive amination reaction; optionally glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

In certain embodiments, the Z moiety is selected from the group consisting of —CH$_2$—(CHOH)— CH$_2$OH, —CH(CH$_2$OH)—[(CHOH)$_{n-1}$]—CH$_2$OH, —CH$_2$OH—CH$_2$—(CHOH)$_2$(CHOR$^3$)(CHOH)—CH$_2$OH, where n is an integer from 3 to 5, and R$^3$ is H or a cyclic or aliphatic monosaccharide. In certain embodiments, the Z-moiety are the glycityls where n is 4, particularly —CH$_2$—(CHOH)$_4$—CH$_2$OH.

In the above formula, R$^1$ can be, for example, N-methyl, N-ethyl, N-propyl, N-isopropyl, N-butyl, N2-hydroxyethyl, N-methoxypropyl or N2-hydroxypropyl. R$^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

In certain embodiments, polyhydroxy fatty acid amides have the general formula:

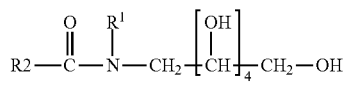

wherein R$^1$ is methyl or methoxypropyl; R$^2$ is a C$_{11}$-C$_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

In certain embodiments, an emulsifier may be useful in solubilizing the immobilizing agent(s) in the emollient. This may be the case for certain of the glucamides such as the N-alkyl-N-methoxypropyl glucamides having HLB values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula CH$_3$(CH$_2$)$_{17}$(OCH$_2$CH$_2$)$_n$ OH, where n has an average value of 2), sorbitan tristearate, isosorbide laurate, and glyceryl monostearate. The emulsifier can be included in an amount sufficient to solubilize the immobilizing agent in the emollient such that a substantially homogeneous mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of Steareth-2 and sorbitan tristearate as the emulsifier.

Other types of ingredients that can be used as immobilizing agents, either alone, or in combination with the above-mentioned immobilizing agents, include waxes such as carnauba, ozokerite, beeswax, candelilla, paraffin, ceresin, esparto, ouricuri, rezowax, isoparaffin, and other known mined and mineral waxes. The high melt point of these materials can help immobilize the composition on the desired surface or location on the article. Additionally microcrystalline waxes are effective immobilizing agents. Microcrystalline waxes can aid in "locking" up low molecular weight hydrocarbons within the skin care composition. In certain embodiments, the wax is a paraffin wax. In certain embodiments, an alternate immobilizing agent is a paraffin wax such as Parrafin S.P. 434 from Strahl and Pitsch Inc. P.O. Box 1098 West Babylon, N.Y. 11704.

The amount of the optional immobilizing agent that can be included in the composition will depend on a variety of factors, including the actives (e.g., emollients) involved, the particular immobilizing agent involved, if any, the other components in the composition, whether an emulsifier is required to solubilize the immobilizing agent in the other components, and like factors. When present, the composition will typically comprise from about 5 to about 90% of the immobilizing agent. Optionally, the composition will comprise from about 5 to about 50%, optionally from about 10 to about 40%, of the immobilizing agent.

Prebiotics/Probiotics

In certain embodiments, the articles of the preset invention further comprise prebiotics and/or probiotics. Probiotics as used herein means those live microorganisms, which when administered in adequate amounts, can confer a health-benefit on a host. Lactic acid bacteria (lactobacillus) and bifidobacteria are the most common types of microbes used as probiotics; but certain yeasts and bacilli may also confer a health benefit.

Bacteria of the Lactobacillus genus are characterized as rod-shaped, gram-positive and non-spore-forming bacteria. Of the family Lactobacillaceae, Lactobacillus inhabit the urogenital tracts of animals and humans and are important members of lactic acid producing group of bacteria. Lactobacillus species suitable for use in the present invention are those which 1.) readily adhere to the epithelial cells of either the urogenital or gastrointestinal tracts of mammals; 2.) produce hydrogen peroxide; 3.) promote low pH; and produce bactefiocins. By "bactefiocins," as used herein, means proteinaceious, bactefiocidal substances synthesized by bacteria, which usually have a narrow spectrum of activity, inhibiting strains of the same or closely related species. Bacteriocins appear to be capable of displacing or suppressing the growth of other bacteria, and as such may provide an advantage to microorganisms in fermenting the female genital tract ecosystem. In certain embodiments, the species of Lactobacillus include *L. acidophilus, L. catenaforme, L. brevis, L. bulgaricus, L. lactis, L. reuterii, L. gasseri, L. helveticus, L. casei, L. plantarum, L. delbrueckii, L. thermophilis, L. jensenii, L crispatus, L. rogosae, L. fermentum* or mixtures thereof. Optionally, the species of Lactobacillus applied to the articles of the present invention include *L. acidophilus, L. casei, L. crispatus, L. fermentum, L. plantarum* or mixtures thereof. Optionally, the Lactobacillus species applied to the articles of the present invention are hydrogen peroxide producing such as *L. acidophilus, L. catenaforme, L. casei, L. crispatus, L. delbrueckii, L. jensenii, L rogosae, L. fermentum, L. gasseri, L. plantarum* mixtures thereof which also exhibit adhesive properties.

Also inhabiting the urogenital tracts of mammals and usefully applied to the articles of the present invention are species of the genus Bifidobacterium (family Actinomyeetaceae). Bifidobacterium species are non-acid-fast, nonmotile gram negative rods. Lactic and acetic acid producing Bifidobacteria are also considered important regulators of the urogenital flora of mammals. In certain embodiments, the Bifidobacterium user herein include, but are not limited to, *B. longum, B. breve, Lactobacillus Bifidus, Lactobacillus bifidus* subsp. *pennsylvanicus* and mixtures thereof. Optionally, the Bifidobacterium species applied to the articles of the present invention include *Lactobacillus Bifidus, Lactobacillus bifidus* subsp. *pennsylvanicus* and mixtures thereof. Mixtures of the Lactobacillus and/or Bifidobacterium species may also be used. Optionally, the probiotics listed above are applied as freeze-dried or lyophilized organisms. Mixtures of any of the above probiotics may also be used.

Also usefully applied to the articles of the present invention are prebiotics. Prebiotics as used herein means non-digestible ingredients that beneficially affect the host by selectively stimulating the growth and/or activity of one or a limited number of generally beneficial bacteria. The prebiotic establishes and maintains the growth of lactic acid bacteria, such as Lactobacillus and/or Bifidobacterium, without facilitating extreme growth of pathogenic bacteria. Examples of suitable prebiotics include, but are not limited to, yeast extracts; gangliosides; salicin; mono-, di- and polysaccharide sugars such as glycogen, glucose, fructose, rhamnose, lactulose, methyl-α-D-mannoside, p-nitrophenol-α-D-mannoside, maltose, maltodextrin, dextrin, dextran, levan, sialic acid and acetylglucosamine as well as oligosaccharides such as, but not limited to, fructooligosaccharides, galactooligosaccharides and soybean oligosaccharides. Fiber or fermentable substrates such as psyllium may be applied to the articles of the present compositions as may gums such as guar gum and xanthum gum. Similarly, proteinacious materials such as, peptone, keratin; vegetable; soy and unsaturated fatty acids such as lauric acid and teichoic acids such as lipoteichoic acid and esters such as glycerophosphates or β-glycerophosphates are also useful as prebiotics. Optionally, the prebiotic includes lactose, lactulose, rhamnose, oligosaccharides, glycogen mixtures thereof.

In certain embodiments, the prebiotic is an oligosaccharide such as, but not limited to, galactooligosaccharides, soybean oligosaccharides and fructooligosaccharides. Oligosaccharides possess bioadhesive properties which help fix the location of these growth factors for easier access by lactic acid bacteria. In certain embodiments, the prebiotic is a fructooligosaccharide. Fructooligosaccharides suitable for use herein may or may not have non-fructosyl units in place of fructosyl end units. The same is true for other oligosaccharides with respect to their osyl end units. Non-fructosyl units may include, but are not limited to, polyalcohols such as xylitol, mannitol, and sorbitol. In certain embodiments, the fructooligosaccharide used herein includes inulin, oligofructose or mixtures thereof. Mixtures of any of the above prebiotics may also be used.

Embossing

In certain embodiments, the articles of the present invention further comprise embossed regions. The embossed regions can be imparted by one or more methods suitable for permanently embossing thin films or film-like material. By way of example only, the compressed regions can be formed using heat and/or pressure as well as other methods such as ultrasonic energy and so forth. As a particular example, compression of selected regions of substrate material 14 of article 10 can be achieved via the use of patterned roller assemblies such as are commonly used in point bonding processes. Point bonding generally refers to the process of mechanically compressing one or more layers at numerous small, discrete points. In certain embodiments, the surface of the substrate material 14 of article 10 is embossed by thermal point bonding which generally involves passing the material (or layer of material) to be bonded between heated rolls such as, for example, an engraved or patterned roll and a second roll. The engraved roll is patterned in some way so that the material (or layer of material) is not bonded over its entire surface, and the second roll can either be flat or patterned. Various patterns for engraved or patterned rolls have been developed for functional as well as aesthetic reasons and, by way of example only, various bond patterns are described in U.S. Pat. No. 3,855,046 to Hansen et al.; U.S. Pat. No. 4,374,888 to Bomslaeger; U.S. Pat. No. 5,635,134 to Bourne et al.; U.S. Pat. No. 5,620,779 to Levy et al.; U.S. Pat. No. 5,714,107 to Levy et al.; U.S. Design Pat. No. 390,798 to Brown; U.S. Pat. No. 5,858,519 to Stokes et al.; and U.S. Design Pat. No. 369, 907 to Sayovitz et al., each of which patents are herein incorporated by reference. Additionally, the polymer film may be microembossed, have a printed design, have a printed message to the consumer, and/or may be at least partially colored.

Color Cues

Concerning color cues, colored lines or regions are optionally added to the articles of the present invention. In certain embodiments, the articles of the present invention may be contain channels (e.g., embossings), and/or specific regions with color, to provide a color cue that is visible to a user when viewing a specified surface of the article 10. The "regions" of colored may correspond in size, shape and location to provided "channels". In certain embodiments, the regions of color are multicolored or in the form of a continuum of a single color (such as, for example, a continuum of various shades of blue). In certain embodiments, the colored regions can provide the user with a color cue to the presence of and/or function of the channels. Any means known to those of skill in the art may be utilized to provide the colored regions such as printing, utilizing colored fibers, or any other suitable means. A more illustrative discussion is provided in US Patent Publication US 20120004633 A1 to Marcelo et al., herein incorporated by reference.

Temperature Change Agents

Concerning temperature change agents, the article 10 of the present invention optionally comprises a temperature change agent that provides a perception of temperature change to the user's skin or mucosal region of the target placement region. For example, in one embodiment, the temperature change agent may comprise an active agent such as a neurosensory agent (i.e., agents that induce a perception of temperature change without involving an actual change in temperature such as, for example peppermint oil, eucalyptol, eucalyptus oil, methyl salicylate, camphor, tea tree oil, ketals, carboxamides, cyclohexanol derivatives, cyclohexyl derivatives, and mixtures thereof).

In another suitable embodiment the temperature change agent comprises a cooling agent. Suitable cooling agents are chemical compounds that have a negative heat of solution; that is, suitable cooling agents are chemical compounds that when dissolved in water feel cool due to an endothermic chemical reaction. Some suitable cooling agents include, for example, ammonium nitrate, sodium chloride, potassium chloride, xylitol, barium hydroxide ($Ba(OH)_2 \cdot 8H_2O$), barium oxide ($BaO \cdot 9H_2O$), magnesium potassium sulfate ($MgSO_4 \cdot K_2SO_4 \cdot 6H_2O$), potassium aluminum sulfate ($KAl(SO_4)_2 \cdot 12H_2O$), sodium borate (tetra) ($Na_2B_4O_7 \cdot 10H_2O$), sodium phosphate ($Na_2HPO_4 \cdot 12H_2O$), and mixtures thereof.

In other suitable embodiments the temperature change agent comprises a heating agent, which includes compounds with an exothermic heat of hydration and compounds with an exothermic heat of solution. Suitable compounds for use as heating agents include, for example, calcium chloride, magnesium chloride, zeolites, aluminum chloride, calcium sulfate, magnesium sulfate, sodium carbonate, sodium sulfate, sodium acetate, metals, slaked lime, quick lime, glycols, and combinations thereof. In certain embodiments, the heating agents may be in either hydrous or anhydrous forms, although anhydrous forms are generally preferred. In certain other embodiments, the compounds include magnesium chloride and calcium chloride.

In other embodiments, the temperature change agent may be capable of activation upon exposure to air, so that no activating agent need be encapsulated with the temperature change agent. Rather, upon rupture of the capsule (or microcapsule) the temperature change agent is exposed to air to induce a temperature change sensation.

Optionally or additionally, the temperature change agent can function as a placement aid to provide a sensory cue to the user such as a real or perceived temperature change. The user can then determine based on the sensory cue whether the article 10 is properly positioned relative to the user. If necessary, the user adjusts the orientation and/or position of the article 10 relative to the user until the sensory cue provided by the placement aid indicates that the article is in the proper position. The rest of the article is then urged against the user so that adhesive on the body-facing surface 16 of substrate material 14 adheres to the user with the article 10 aligned with the vaginal region of the user to secure the article 10 in the proper position on the wearer.

In certain embodiments, the temperature change agent functions as an indicator to alert the user of the need to replace the article 10 with a new article 10.

Application/Removal Aids

The article 10 may also be provided with a removal or application aid which provides the user with an easy way to grasp and apply the article or remove the article once applied to the body. In certain embodiments, the removal aid can be a tab or a wing positioned on either, or both of, the front, back or the sides of the article to aid application and/or removal of the article. In one embodiment, the application/removal aid is a tab or wing located on at least one end of article 10 which is not adhered to the body or is devoid of adhesive or other attachment means. Alternatively, other application/removal aids, such as having an area or portion of body-facing surface 16 of the substrate material 14 at least one end of article 10 being devoid of the adhesive 20. Other types of application/removal aids which may be present include loops, and pull strings. In certain embodiments, the article 10 has a three dimensional (or non-flat) surface which allows for easier application and/or better fit. In certain other embodiments, the article has areas on the surface which are tactile (or which have tactile features) to aid in the placement of the article. In an embodiment, the article has finger pouches (e.g., pockets arranged so as to receive a finger of the user) for aiding application and/or removal of the article. Optionally, when removing the article, the removal aid allows the user to effectively begin the process of gently removing the article from the body of the user, without the need of having to find a portion of the article which may not be completely attached. Examples of "tab" application delivery systems can be found in U.S. Pat. No. 5,088,483 to Heinecke, filed Mar. 20, 1991, the specific disclosure of which materials is found in FIGS. 1-5 and at col. 3, line 41 to col. 4, line 55 and is herein incorporated by reference; in addition to the foregoing, the remainder of U.S. Pat. No. 5,088,483 is also herein incorporated by reference. Examples of alternative application delivery systems can be found in FIGS. 1-8 and col. 1, line 50 to col. 2, line 45 of U.S. Pat. No. 4,372,303 to Grossmann et al., filed Sep. 11, 1980; FIGS. 1-11 and col. 2, line 46 to col. 5, line 25 of U.S. Pat. No. 4,513,739 to Johns, filed Feb., 15, 1983; FIGS. 1-5 and col. 2, line 22 to col 5, line 38 of U.S. Pat. No. 4,485,809 to Dellas, filed Dec. 11, 1981, the indicated portions of which patents are herein incorporated by reference; in addition to the foregoing, the remaining portion of each of U.S. Pat. Nos. 4,372,303; 4,513,739 and 4,485,809 is also herein incorporated by reference. Also useful as an application/removal aid are the "gripping section" and "carrier system" of U.S. Pat. No. 7,880,051 to Madsen et al., the specific disclosure of which materials is found in FIGS. 1-42; at col. 5, line 38 to col. 7, line 21; and at col. 11, line 45 to col. 18, line 58, which disclosure is herein incorporated by reference; in addition to the foregoing, the remainder of U.S. Pat. No. 7,880,051 is also herein incorporated by reference.

Method of Operation

In certain embodiments, the articles of the present invention are applied as follows:

Before beginning the application process, the user should be relaxed and calm and the hands of the user should be clean. To begin the application process, it is recommended that the user sit on a toilet with knees apart. The area on the user for application of the article should be dry. The article of the present invention should be removed from its packaging and any removable release liners or backing removed. The area of the labia should be manipulated by the user such that the labia minora is in a closed configuration. While maintaining the closed configuration of the labia minora, the body facing surface with attachment means (e.g., adhesive) is positioned to cover the labia region and maintain the labia minora in a closed configuration. The article is manipulated to secure and seal attachment by attachment means to the user's body.

In certain embodiments, the article is removed as follows:

Before beginning the removal process, the user should be relaxed and calm and the hands of the user should be clean. To begin the removal process, the user will sit on the toilet with knees apart. The applied article is wiped with a substrate (e.g., toilet tissue or wipe). The article is removed by contacting and pulling on the removal aid so as initiate removal of the article and then pulling the article off. Excess vaginal exudate on the body or existing the body is removed using an absorbent article (e.g., washcloth or absorbent paper towel). The absorbent article also dries area on the user for application of a new (or fresh) article of the present invention. The new article of the present invention is applied as described above. The frequency of application of the articles of the present invention, optionally, range from twice daily (or optionally three times daily) to 20 times daily (or optionally from 10 times daily).

EXAMPLES

The articles of the present invention as described in following examples illustrate specific embodiments of articles of the present invention, but are not intended to be limiting thereof. While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of the invention.

Example I-a Labial Adhesive Patch

A labial adhesive patch is made by coating a 100 mm long by 100 mm wide, microporous polyethylene film grade 19 gsm BR-134U white breathable film, from Clopay, Mason, Ohio, with 30 mg/sq inch of two-part adhesive MG 7-9800 Soft Skin Adhesive Kit (A & B) from Dow Corning®, Midland, MI The labial adhesive patch is laminated to release coated POLY SLIK® brand paper, available from Loparex Inc., Willowbrook, Ill. The labial adhesive patch is individually packaged. The consumer opens the package, removes the product, peels away the release paper and applies the article (adhesive side towards the body) to the body such that the center of the article is aligned with the user's vaginal opening and the labia minora is maintained in a closed configuration. The product retains menstrual fluid within the vagina.

Example II—an Inner Labial Patch

A inner labial patch is prepared by coating a 20 mm long by 20 mm wide, 0.2 mm thick Type 625 polyurethane film, from J. P. Stevens, with 30 mg/sq inch of two-part adhesive MG 7-9800 Soft Skin Adhesive Kit (A & B) from Dow Corning®, Midland, MI The patch is laminated to a release coated POLY SLIK® brand paper, available from Loparex Inc., Willowbrook, Ill. and individually packaged. The consumer opens the package, removes the product, peels away the release paper and applies the product (adhesive side towards the body) internal to the labia, but external to the vagina, so that the inner labial patch is applied directly over the introitus. The product retains menstrual fluid within the vagina.

We claim:

1. An article for maintaining menstrual fluid within a vagina having labia minora, the article comprising:
 a flexible, elastic polymer film substrate having a body facing surface, an opposed garment facing surface, and a perimeter;
 adhesive applied in a closed pattern to the entire perimeter of the body facing surface of the substrate and arranged and configured to extend over about 5% to about 80% of the body facing surface of the substrate to sealingly attach to the labia minora of the body to maintain menstrual fluid within the vagina; and
 wherein (1) the substrate has a length as measured along a longitudinally extending centerline of about 20 mm to about 150 mm, a width as measured along a transversely extending centerline of about 20 mm to about 100 mm, (2) the article has a total fluid capacity of less than 3.0 g, (3) a shear force required to remove the adhesive from skin is greater than a force required to deform the substrate, and (4) the article is free to move with the body during use and recover its original shape while maintaining an adhesive seal to the labia minora of the body.

2. The article according to claim 1, wherein the substrate is structured and arranged to extend at least from one labium minus to an opposed labium minus.

3. The article according to claim 2, wherein the article has a total fluid capacity of less than 0.1 g.

4. The article according to claim 1, wherein the article has a thickness in the range of about 0.1 mm to about 5 mm.

5. The article according to claim 1, wherein the article has a total surface area in a range of about 400 mm$^2$ to about 15000 mm$^2$.

6. The article according to claim 1, wherein the adhesive has the following properties:
$$G'_{[100\ rad/sec@37°\ C.]}/G'_{[0.1\ rad/sec@37°\ C.]} \geq 4.5;\text{ and}$$
$$-20°\ C. \leq Tg\ (°\ C.) \leq 15°\ C.$$

7. The article according to claim 1, wherein the adhesive has a peel force of from about 100 to about 700 N/m.

8. The article according to claim 1, wherein the article has a Gurley stiffness of from 2 mg to 5 mg.

9. The article according to claim 1, wherein the article has a Fluid Penetration Time (FPT) of greater than 500 seconds.

10. An article for maintaining menstrual fluid within a vagina having labia minora, the article comprising:
 a flexible, elastic polymer film substrate having a body facing surface, an opposed garment facing surface, and a perimeter;
 an adhesive selected from the group consisting of non-pressure sensitive adhesive substance, muco- or bioadhesive or mixtures thereof wherein the adhesive is applied in a closed pattern to the entire perimeter of the body facing surface of the substrate and arranged and configured to extend over about 5% to about 80% of the body facing surface of the substrate to sealingly attach to the labia minora of the body to maintain menstrual fluid within the vagina; and
 wherein (1) the article has a length as measured along a longitudinally extending centerline of about 20 mm to about 150 mm, a width as measured along a transversely extending centerline of about 20 mm to about 100 mm, and is sized, structured and arranged to fit in the region on the internal side of the labia but external the vagina, (2) the article has a total fluid capacity of less than 3.0 g, (3) a shear force required to remove the adhesive from skin is greater than a force required to deform the substrate, and (4) the article is free to move with the body during use and recover its original shape while maintaining an adhesive seal to the labia minora of the body.

11. The article according to claim 10 wherein the adhesive is a non-pressure sensitive adhesive substance.

12. The article of claim 11 wherein the non-pressure sensitive adhesive substance is selected from the group consisting of waxes, fatty alcohols, high molecular weight alcohols, fatty acids, petroleum jelly, sealing ointments, non-ionic surfactants, alkoxylated amide, alkoxylated amines, alkyl amido alkyl amines, alkyl substituted amino acids, sucrose fatty acid esters and mixtures thereof.

13. The article according to claim 10 wherein the adhesive is a muco- or bioadhesive.

14. The article according to claim 13 wherein the muco- or bioadhesive selected from the group consisting of selected from the group consisting of natural, synthetic or biological polymers, lipids, phospholipids, silicone adhesive gels and mixtures thereof.

15. The article according to claim 14 wherein the muco- or bioadhesive is a natural and/or synthetic polymer selected from the group consisting of cellulosic derivatives, natural gums, polyacrylates, alginates, polyoxyethylenes, polyethylene glycols (PEG), dextrans, block copolymers and mixtures thereof.

16. The article according to claim 14 wherein the muco- or bioadhesive is a silicone adhesive gel in the form of silicone gel adhesive precursors.

17. The article according to claim 10, wherein the article has a Gurley stiffness of from 2 mg to 5 mg.

\* \* \* \* \*